United States Patent
Van Wijk

(10) Patent No.: US 10,166,252 B2
(45) Date of Patent: Jan. 1, 2019

(54) METHOD FOR ASSESSING AND TREATING OR PREVENTING IMPAIRED PLASMA POLAR LIPID LEVELS

(71) Applicant: N.V. Nutricia, Zoetermeer (NL)

(72) Inventor: Nick Van Wijk, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 15/303,592

(22) PCT Filed: Apr. 14, 2015

(86) PCT No.: PCT/NL2015/050244
§ 371 (c)(1),
(2) Date: Oct. 12, 2016

(87) PCT Pub. No.: WO2015/160247
PCT Pub. Date: Oct. 22, 2015

(65) Prior Publication Data
US 2017/0027979 A1    Feb. 2, 2017

(30) Foreign Application Priority Data

Apr. 14, 2014  (WO) ................ PCT/NL2014/050233
May 23, 2014  (EP) ..................................... 14169740

(51) Int. Cl.
| | |
|---|---|
| *A61K 31/70* | (2006.01) |
| *A61K 31/44* | (2006.01) |
| *A61K 31/355* | (2006.01) |
| *A61K 31/34* | (2006.01) |
| *A61K 31/20* | (2006.01) |
| *A61K 31/714* | (2006.01) |
| *A61K 31/095* | (2006.01) |
| *A61K 31/14* | (2006.01) |
| *A61K 31/202* | (2006.01) |
| *A61K 31/375* | (2006.01) |
| *A61K 31/4415* | (2006.01) |
| *A61K 31/519* | (2006.01) |
| *A61K 31/7072* | (2006.01) |
| *A61K 45/06* | (2006.01) |

(52) U.S. Cl.
CPC .......... *A61K 31/714* (2013.01); *A61K 31/095* (2013.01); *A61K 31/14* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/7072* (2013.01); *A61K 45/06* (2013.01)

(58) Field of Classification Search
CPC ...... A61K 31/714; A61K 31/44; A61K 31/20; A61K 31/355; A61K 31/375
USPC .................. 514/52, 345, 356, 458, 474, 560
See application file for complete search history.

(56) References Cited

FOREIGN PATENT DOCUMENTS

| | | |
|---|---|---|
| EP | 1 800 675 A1 | 6/2007 |
| WO | WO-2009/002146 A1 | 12/2008 |
| WO | WO-2012/091542 A1 | 7/2012 |

OTHER PUBLICATIONS

Douaud, et al., PNAS, vol. 110, No. 23 Jun. 4, 2014, (pp. 9523-9528). (Year: 2014).*
Durga et al., The Lancet, vol. 369, pp. 208-216, Jan. 20, 2007. (Year: 2007).*
Sperling et al., (Alzheimer's & Dementia, vol. 7: pp. 280-292 (2011)). (Year: 2011).*
Anonymous: "Neu bei Alzheimer-Krankheit im Fruhstadium: Medizinische Ernahrung als vielverzsprechendes Therapiekonzept (BILD)", 2013, retrieved from the Internet: URL:http://www.presseportal.de/pm/29412/2477178/neu-bei-alzheimer-krankheit-im-fruehstadium-medizinische-ernaehrung-als-vielversprechendes.
Anonymous: "Souvenaid", retrieved from the Internet on Jul. 17, 2014: URL:http://www.nutricia.de/productpdf/PN_Souvenaid_20199.pdf.
Kamphius et al., "Nutrition and Alzheimer's disease: pre-clinical concepts", European Journal of Neurology, 2009, vol. 16 (Suppl. 1), pp. 12-18.
Mapstone et al., "Plasma phospholipids identify antecedent memory impairment in older adults", Nature Medicine, 2014, vol. 20, retrieved from the internet: URL:http://www.nature.com/nm/journal/v20/n4/full/nm.3466.html.
Scheltens et al., "Efficacy of a medical food in mild Alzheimer's disease: A randomized controlled trial", Alzheimer's and Dementia, 2010, vol. 6, pp. 1-10.
Van Wijk et al., "Plasma choline concentration varies with different dietary levels of vitamins B6r B12 and folic acid in rats maintained on choline-adequate diets", British Journal of Nutrition, 2012, vol. 107, pp. 1408-1412.
Wurtman et al., "Nutritional modifiers of aging brain function: use of uridine and other phosphatide precursors to increase formation of brain synapses", Nutrition Reviews, 2010, vol. 68 (Suppl. 2), pp. S88-S101.
International Search Report issued in International Patent Application No. PCT/NL2015/050244, dated Jul. 30, 2015.

(Continued)

*Primary Examiner* — Raymond J Henley, III
(74) *Attorney, Agent, or Firm* — Gilberto M. Villacorta; Sunit Talapatra; Foley & Lardner LLP

(57) ABSTRACT

The invention pertains to the use of a preparation for the manufacture of a composition for preventing or treating impaired plasma levels of one or more polar lipids such as phosphatidylcholines [PC] selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a preclinical AD or MCI subject or a subject with a high likelihood of developing AD or MCI, and wherein said subject is administered with a composition comprising at least one, preferably at least two, most preferably all B vitamins selected from the group consisting of vitamin B6, vitamin B12 and vitamin B9.

29 Claims, No Drawings

(56) References Cited

OTHER PUBLICATIONS

Written Opinion of the International Searching Authority issued in International Patent Application No. PCT/NL2015/050244, dated Jul. 30, 2015.

* cited by examiner

METHOD FOR ASSESSING AND TREATING OR PREVENTING IMPAIRED PLASMA POLAR LIPID LEVELS

CROSS-REFERENCE TO RELATED APPLICATIONS

This application is the National Phase of International Patent Application No. PCT/NL2015/050244, filed Apr. 14, 2015, published on Oct. 22, 2015 as WO 2015/160247 A1, which claims priority to European Patent Application No. 14169740.9, filed May 23, 2014 and to International Patent Application No. PCT/NL2014/050233, filed Apr. 14, 2014. The contents of these applications are herein incorporated by reference in their entirety.

FIELD OF THE INVENTION

The invention is in the field of medical nutrition and more particularly relates to a composition for use in preventing or treating impaired plasma polar lipid levels, preferably specific phosphatidylcholine (PC) levels in a preclinical Alzheimer's Disease [AD] or mild cognitive impairment [MCI] subject or a subject with a high likelihood of developing AD or MCI.

BACKGROUND DESCRIPTION

In the art there is a need for detecting neurodegenerative disorders and particularly AD already in pre-clinical stages, before AD symptoms such as cognitive dysfunction can be diagnozed. Amyloid plaques and neurofibrillary tangles, the neuropathological hallmarks of AD, are not limited to individuals with dementia. Preclinical subjects also encompass those not suffering from amyloid plaques or neurofibrillary tangles. Pathologic changes can also be present in the brains of cognitively normal older adults—a condition that is commonly defined as preclinical AD. Similar definitions hold for preclinical MCI. Reference is made to Sperling et at. "*Toward defining the preclinical stages of Alzheimer's disease: Recommendations from the National Institute on Aging-Alzheimer's Association workgroups on diagnostic guidelines for Alzheimer's disease*" Alzheimer's & Dementia 9 (2011) 280-292; the contents hereof incorporated by reference. This way such subjects could specifically be targeted at much earlier stages. The art is searching for ways to identify and treat such preclinical subjects as early as possible.

Subjects, including preclinical AD or MCI subjects, suffering from impaired plasma polar lipid levels, preferably PC levels have an extremely high likelihood of developing mild cognitive impairment and Alzheimer's Disease. For some phospholipids, impaired levels can be associated with a 90% likelihood of developing such pathological conditions, long before symptoms such as cognitive dysfunction could even be diagnosed.

Advantageously, monitoring for changes in plasma phospholipid levels, preferably PC levels does not require any tedious brain imaging techniques such as electroencephalography (EEG).

SUMMARY OF THE INVENTION

Through clinical studies the inventors established a set of biomarkers of plasma polar lipid species, preferably phosphatidylcholine [PC] species, which help identifying subjects suffering from impaired levels of these plasma phospholipids, at the basis of which impaired phospholipid levels a subject can be identified having an extremely high likelihood of developing MCI and AD. These biomarkers are thus reliably predictive for conversion of a subject to MCI and AD, and help identifying ant treating preclinical MCI and AD subjects.

In addition, the inventors found that impaired plasma phospholipid levels could be normalized using B vitamins only. Also, B vitamins helped preventing the plasma levels of a set of polar lipids, preferably a set of phospholipids from changing. In a further intervention study of 24 weeks involving administration of a product comprising B vitamins to a subject suffering from mild AD it was found that impaired plasma phospholipid levels could be normalized.

In one leg of experiments, the biomarker panel of phospholipids studied involved impaired plasma levels of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6]. The increase in plasma levels of these phospholipids was most profound. In one aspect, the preferred targeted plasma polar lipids comprise one or more selected from phosphatidylcholine species with multiple double bonds, preferably selected from the group consisting of 36:6, 38:6, 40:6, more preferably at least two of these polyunsaturated PC species. The invention is particularly directed to treating or preventing impaired plasma levels of at least PC aa 40:6 and/or PC ae 40:6, most preferably at least PC aa 40:6.

In a second leg of experiments, the biomarker panel of phospholipids studied involved a more expanded set of plasma polar lipids also including phosphatidylcholine (PC) species, levels of which plasma polar lipid species were changed significantly through intervention with B vitamins. For some, these effects were also confirmed using B vitamins in combination with further components.

Based on all those experimental observations, the nutritional intervention is believed useful in treating preclinical subjects with plasma lipid biomarker profiles predictive for conversion to preclinical MCI or AD. The studies provided support that the plasma levels of a specific set of phospholipids, as outlined in the application, are indicative of the changes taking place in the brains of cognitively normal older adults and prodromal AD or MCI subjects. The inventors observed that intervention with a composition comprising therapeutically effective amounts of B vitamin(s) helped treating or restoring these impaired plasma polar lipid levels, and also helped preventing an undesired change of these plasma polar lipid levels in subjects prone to developing AD or MCI, particularly preclinical subjects. Preclinical MCI and preclinical AD subjects are defined in the art represented by Sperling Alzheimer's & Dementia 9 (2011) 280-292, incorporated by reference. As evident from FIG. 3 therein, in the preclinical stages the subject may be identified through all kinds of biomarkers but show low cognitive dysfunction. These subjects have an increased likelihood of developing into MCI and AD subjects, accompanied from increased cognitive dysfunction.

Based on the experimental findings presented herein it is concluded that a change of the plasma concentrations in each of the individual polar lipid species, particularly PC species is already indicative of an improved biomarker profile. It is not deemed necessary to monitor the plasma levels of each of these polar lipid species, particularly PC species in order to draw any conclusions on the extent of impairment and treatment.

List of Preferred Embodiments I
1. Use of a preparation for the manufacture of a composition for preventing or treating impaired plasma levels of one or more phosphatidylcholines [PC] selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a preclinical AD or MCI subject or a subject with a high likelihood of developing AD or MCI, and wherein said subject is administered with a composition comprising at least one, preferably at least two, most preferably all B vitamins selected from the group consisting of vitamin B6, vitamin B12 and vitamin B9.
2. Use according to embodiment 1, said composition comprising per daily dosage or per 100 ml, at least one, preferably at least two, most preferably all of:
0.5-10000 μg, preferably 0.5 -1000 μg vitamin B12;
0.5-100 mg, preferably 0.7-20 mg vitamin B6; and
100-5000 μg, preferably 150-1000 μg folic acid.
3. Use according to embodiment 1 or 2, said composition comprising per daily dosage or per 100 ml, 0.5 -100 mg, preferably 0.7-20 mg vitamin B6, and 100 -5000 μg, preferably 150-1000 μg folic acid.
4. Use according to any one of the preceding embodiments, wherein said one or more phosphatidylcholines involve at least two, more preferably at least three phosphatidylcholine species selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6].
5. Use according to any one of the preceding embodiments, wherein said one or more phosphatidylcholine species is selected from the group consisting of phosphatidylcholine diacyl C36:6 [PC aa C36:6], phosphatidylcholine diacyl C38:6 [PC aa C38:6], phosphatidylcholine diacyl C40:6 [PC aa C40:6] and phosphatidylcholine acyl-alkyl C40:6 [PC ae C40:6], preferably at least phosphatidylcholine diacyl C40:6 [PC aa C40:6] and/or phosphatidylcholine acyl-alkyl C40:6 [PC ae C40:6].
6. Use according to any one of the preceding embodiments, wherein said plasma PC levels are monitored in said subject before and/or after administration.
7. Use according to any one of the preceding embodiments, wherein said composition further comprises one or more of uridine and cytidine, or salts, phosphates, acyl derivatives or esters thereof.
8. A method for preventing or treating impaired plasma PC levels in a preclinical AD or MCI subject or a subject with a high likelihood of developing AD or MCI, comprising:
a) analyzing plasma levels of at least one phospholipid in a subject;
b) selecting a subject having an impaired plasma level of one or more PC species selected from the group consisting of phosphatidylcholine diacyl C36:6 [PC aa C36:6], PC aa C38:0, PC aa C38:6, PC aa C40:6 and PC acyl-alkyl C40:6 [PC ae C40:6];
c) administering to said selected subject a composition comprising at least one, preferably at least two, most preferably all B vitamins selected from the group consisting of vitamin B6, vitamin B12 and vitamin B9, and optionally one or more of uridine and cytidine, or salts, phosphates, acyl derivatives or esters thereof.
9. The method according to embodiment 8, wherein said plasma PC levels are monitored after administration of said composition.
10. The method according to embodiment 8 or 9, wherein said subject is selected having impaired plasma levels of one or more phosphatidylcholine species selected from the group consisting of phosphatidylcholine diacyl C36:6 [PC aa C36:6], phosphatidylcholine diacyl C38:6 [PC aa C38:6], phosphatidylcholine diacyl C40:6 [PC aa C40:6] and phosphatidylcholine acyl-alkyl C40:6 [PC ae C40:6], preferably at least phosphatidylcholine diacyl C40:6 [PC aa C40:6] and/or phosphatidylcholine acyl-alkyl C40:6 [PC ae C40:6].
11. Use or method according to any one of the preceding embodiments, wherein said composition further comprises a lipid fraction comprising at least one of docosahexaenoic acid (22:6; DHA), eicosapentaenoic acid (20:5; EPA) and docosapentaenoic acid (22:5; DPA), or esters thereof.
12. Use or method according to any one of the preceding embodiments, wherein said composition further comprises, per daily dose or preferably per 100 ml composition, at least 500 mg of DHA, preferably at least 600 mg of DHA, and at least 50 mg of uridine, preferably at least 100 mg of uridine.
13. Use or method according to any one of the preceding embodiments, wherein the composition comprises, per daily dose or preferably per 100 ml composition:
0.5-10000 μg, preferably 0.5-1000 μg vitamin B12;
0.5-100 mg, preferably 0.7-20 mg vitamin B6;
100-5000 μg, preferably 150-1000 μg folic acid;
100-500 mg, preferably 200-400 mg EPA,
1000-1500 mg, preferably 1100-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 70-90 mg vitamin C, and
40-80 μg, preferably 50-70 μg selenium.
14. Use or method according to any one of the preceding embodiments, wherein the subject is an elderly of at least 50 years of age, and not suffering from any cognitive deficits.
15. A composition for use in for preventing or treating impaired plasma levels of one or more phosphatidylcholines [PC] selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a preclinical AD or MCI subject or a subject with a high likelihood of developing AD or MCI, wherein said subject is administered with a composition comprising at least one, preferably at least two, most preferably all B vitamins selected from the group consisting of vitamin B6, vitamin B12 and vitamin B9.
16. The composition for use according to embodiment 15, further comprising one or more of uridine and cytidine, or salts, phosphates, acyl derivatives or esters thereof.
17. The composition for use according to embodiment 15 or 16, wherein said one or more phosphatidylcholines involve at least two, more preferably at least three phosphatidylcholine species selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6].
18. The composition for use according to any of embodiments 15 -17, wherein said impaired plasma polar lipid levels involve impaired plasma levels of at least one phosphatidylcholine species selected from the group consisting of PC aa C36:6, PC aa C38:6, PC aa C40:6 and PC ae C40:6, preferably at least PC aa C40:6 and/or PC ae C40:6.

List of Preferred Embodiments II
1. Use of a preparation for the manufacture of a composition for preventing or treating impaired plasma levels of one or more polar lipids selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); lPE(22:6); PE(38:6); PE(40:6); PI(38:6); PC(40:7); PC(40:8); PC(42:10); PC(42:7); PC(42:8); PC(42:9); PE(40:7); lPC(22:6); C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5) in a preclinical AD or MCI subject or a subject with a high likelihood of developing AD or MCI, wherein said composition comprises at least one, preferably at least two, most preferably all B vitamins selected from the group consisting of vitamin B6, vitamin B12 and vitamin B9.
2. Use of a preparation for the manufacture of a composition for preventing or treating impaired plasma levels of one or more phosphatidylcholines [PC] selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a preclinical AD or MCI subject or a subject with a high likelihood of developing AD or MCI, and wherein said subject is administered with a composition comprising at least one, preferably at least two, most preferably all B vitamins selected from the group consisting of vitamin B6, vitamin B12 and vitamin B9.
3. Use according to embodiment 1 or 2, said composition comprising per daily dosage or per 100 ml, at least one, preferably at least two, most preferably all of:
0.5-10000 µg, preferably 0.5 -1000 µg vitamin B12;
0.5-100 mg, preferably 0.7-20 mg vitamin B6; and
100-5000 µg, preferably 150-1000 µg folic acid.
4. Use according to embodiment 1-3, said composition comprising per daily dosage or per 100 ml, 0.5 -100 mg, preferably 0.7-20 mg vitamin B6, and 100 -5000 µg, preferably 150-1000 µg folic acid.
5. Use according to embodiment 1 or 2, wherein the plasma polar lipids are lPC 22:6 and/or PC 40:6, preferably at least lPC 22:6.
6. Use according to any one of the preceding embodiments, wherein said one or more phosphatidylcholines involve at least two, more preferably at least three phosphatidylcholine species selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6].
7. Use according to any one of the preceding embodiments, wherein said one or more phosphatidylcholine species is selected from the group consisting of phosphatidylcholine diacyl C36:6 [PC aa C36:6], phosphatidylcholine diacyl C38:6 [PC aa C38:6], phosphatidylcholine diacyl C40:6 [PC aa C40:6] and phosphatidylcholine acyl-alkyl C40:6 [PC ae C40:6], preferably at least phosphatidylcholine diacyl C40:6 [PC aa C40:6] and/or phosphatidylcholine acyl-alkyl C40:6 [PC ae C40:6].
8. Use according to any of the preceding embodiments, wherein said plasma PC levels are monitored in said subject before and/or after administration.
9. Use according to any one of the preceding embodiments, wherein said composition further comprises one or more of uridine and cytidine, or salts, phosphates, acyl derivatives or esters thereof.
10. A method for preventing or treating impaired plasma PC levels in a preclinical AD or MCI subject or a subject with a high likelihood of developing AD or MCI, comprising:
  a) analyzing plasma levels of at least one phospholipid in a subject;
  b) selecting a subject having an impaired plasma level of one or more PC species selected from the group consisting of phosphatidylcholine diacyl C36:6 [PC aa C36:6], PC aa C38:0, PC aa C38:6, PC aa C40:6 and PC acyl-alkyl C40:6 [PC ae C40:6];
  c) administering to said selected subject a composition comprising at least one, preferably at least two, most preferably all B vitamins selected from the group consisting of vitamin B6, vitamin B12 and vitamin B9, and optionally one or more of uridine and cytidine, or salts, phosphates, acyl derivatives or esters thereof.
11. The method according to embodiment 10, wherein said plasma PC levels are monitored after administration of said composition.
12. The method according to embodiment 10 or 11, wherein said subject is selected having impaired plasma levels of one or more phosphatidylcholine species selected from the group consisting of phosphatidylcholine diacyl C36:6 [PC aa C36:6], phosphatidylcholine diacyl C38:6 [PC aa C38:6], phosphatidylcholine diacyl C40:6 [PC aa C40:6] and phosphatidylcholine acyl-alkyl C40:6 [PC ae C40:6], preferably at least phosphatidylcholine diacyl C40:6 [PC aa C40:6] and/or phosphatidylcholine acyl-alkyl C40:6 [PC ae C40:6].
13. Use or method according to any one of the preceding embodiments, wherein said composition further comprises a lipid fraction comprising at least one of docosahexaenoic acid (22:6; DHA), eicosapentaenoic acid (20:5; EPA) and docosapentaenoic acid (22:5; DPA), or esters thereof.
14. Use or method according to any one of the preceding embodiments, wherein said composition further comprises, per daily dose or preferably per 100 ml composition, at least 500 mg of DHA, preferably at least 600 mg of DHA, and at least 50 mg of uridine, preferably at least 100 mg of uridine.
15. Use or method according to any one of the preceding embodiments, wherein the composition comprises, per daily dose or preferably per 100 ml composition:
0.5-10000 µg, preferably 0.5 -1000 µg vitamin B12;

0.5-100 mg, preferably 0.7-20 mg vitamin B6;
100-5000 µg, preferably 150-1000 µg folic acid;
100-500 mg, preferably 200-400 mg EPA,
1000-1500 mg, preferably 1100-1300 mg DHA,
50-600 mg, preferably 60-200 mg phospholipids,
200-600 mg, preferably 300-500 mg choline,
400-800 mg, preferably 500-700 mg UMP (uridine monophosphate),
20-60 mg, preferably 30-50 mg vitamin E (alpha-TE),
60-100 mg, preferably 70-90 mg vitamin C, and
40-80 µg, preferably 50-70 µg selenium.

16. Use or method according to any one of the preceding embodiments, wherein the subject is an elderly of at least 50 years of age, and not suffering from any cognitive deficits.

17. A composition for use in for preventing or treating impaired plasma levels of one or more polar lipids selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC(22:6); C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5) in a preclinical AD or MCI subject or a subject with a high likelihood of developing AD or MCI, and wherein said subject is administered with a composition comprising at least one, preferably at least two, most preferably all B vitamins selected from the group consisting of vitamin B6, vitamin B12 and vitamin B9.

18. A composition for use in for preventing or treating impaired plasma levels of one or more phosphatidylcholines [PC] selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a preclinical AD or MCI subject or a subject with a high likelihood of developing AD or MCI, wherein said subject is administered with a composition comprising at least one, preferably at least two, most preferably all B vitamins selected from the group consisting of vitamin B6, vitamin B12 and vitamin B9.

19. The composition for use according to embodiment 17 or 18, further comprising one or more of uridine and cytidine, or salts, phosphates, acyl derivatives or esters thereof.

20. The composition for use according to embodiment 17-19, wherein the plasma polar lipids are lPC 22:6 and/or PC 40:6, preferably at least lPC 22:6.

21. The composition for use according to embodiment 17-20, wherein said one or more phosphatidylcholines involve at least two, more preferably at least three phosphatidylcholine species selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6].

22. The composition for use according to any of embodiments 17-21, wherein said impaired plasma polar lipid levels involve impaired plasma levels of at least one phosphatidylcholine species selected from the group consisting of PC aa C36:6, PC aa C38:6, PC aa C40:6 and PC ae C40:6, preferably at least PC aa C40:6 and/or PC ae C40:6.

23. A method for preventing or treating impaired plasma polar lipid levels in a preclinical AD or MCI subject or a subject with a high likelihood of developing AD or MCI, comprising:
    a) analyzing plasma levels of at least one plasma polar lipid in a subject, wherein said plasma polar lipid is selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC(22:6); C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5);
    b) selecting a subject having an impaired plasma level of one or more of said plasma polar lipids;
    c) administering to said selected subject a composition comprising at least one, preferably at least two, most preferably all B vitamins selected from the group consisting of vitamin B6, vitamin B12 and vitamin B9, and optionally one or more of uridine and cytidine, or salts, phosphates, acyl derivatives or esters thereof.

DETAILED DESCRIPTION OF THE INVENTION

In one aspect, the invention pertains to the use of a preparation for the manufacture of a composition for treating (preferably ameliorating or normalizing) or preventing impaired plasma polar lipid levels, preferably phospholipid levels in a preclinical AD or MCI subject or a subject with a high likelihood of developing AD or MCI, wherein said subject is administered with a composition comprising at least one, preferably at least two, most preferably all B vitamins selected from the group consisting of vitamin B6, vitamin B12 and vitamin B9. The composition preferably further comprises one or more of uridine and cytidine, or salts, phosphates, acyl derivatives or esters thereof.

In a second aspect, the invention pertains to a method for treating (preferably ameliorating or normalizing) or preventing impaired plasma polar lipid levels, preferably phospholipid levels in a preclinical AD or MCI subject or a subject with a high likelihood of developing AD or MCI, comprising:

a) analyzing plasma levels of at least one phospholipid in a subject;

b) selecting a subject having an impaired plasma phospholipid level, preferably an impaired plasma phosphatidylcholine level, preferably an impaired plasma level of one or more phosphatidylcholine species selected from the group consisting of phosphatidylcholine diacyl C36:6 [PC aa C36:6], PC aa C38:0, PC aa C38:6, PC aa C40:6 and PC acyl-alkyl C40:6 [PC ae C40:6];

c) administering to said selected subject a composition comprising at least one, preferably at least two, most preferably all B vitamins selected from the group consisting of vitamin B6, vitamin B12 and vitamin B9, and optionally one or more of uridine and cytidine, or salts, phosphates, acyl derivatives or esters thereof.

Treatment of impaired polar lipid levels preferably involves ameliorating or normalizing said levels. With ameliorating or normalizing impaired phospholipid metabolism it is preferably understood that the (impaired) plasma levels of at least 1, preferably at least 2, more preferably at least 3 polar lipid levels, preferably phosphatidylcholine species, even more preferably at least 4 polar lipid levels, preferably phosphatidylcholine species monitored in said subject during intervention are changed significantly, preferably with at least 2% more preferably at least 4%, even more preferably at least 6%, particularly at least 8%, especially at least 10%, more preferably at least 15%, most preferably at least 20%, compared to the impaired levels prior to intervention. Also, prevention of impaired plasma phospholipid levels preferably means that plasma levels of the phospholipids are maintained at normal range, preferably involving changes of less than 20%, preferably less than 15%, preferably less than 10%, more preferably less than 8%, even more preferably less than 5%, most preferably less than 5% of normal values. The prevention or treatment of impaired plasma levels preferably concerns at least the polar lipid levels, preferably PC species specifically mentioned in the application. The invention particularly relates to treatment of impaired plasma polar lipid levels. Abnormalities in these plasma polar lipid levels, preferably PC levels can be assessed by either taking the average values for those plasma levels determined correspondingly a healthy subject (of similar age) (so matched for e.g. age; not diagnosed with any neurological disorder or preclinical AD or MCI) as a reference, and comparing the subject's condition with the reference situation.

In a prefered embodiment, the treatment invokes an increase in these polar lipid levels, preferably PC levels, thus providing a solution to reduced plasma levels. The terminology 'reduced plasma levels' and 'depleted plasma levels' are considered interchangeably, which are readily assessed by skilled artisan.

In particular, in the context of the invention deficits or abnormalities in said plasma polar lipid species, preferably PC levels imply a change in plasma levels of preferably at least 2% change, more preferably at least 4% change, even more preferably at least 6% change, particularly at least 8% change, especially at least 10% change, more preferably at least 15% change, most preferably at least 20% change, compared to the value as determined correspondingly in a healthy individual (of similar age). In one embodiment, the above change is preferably a decrease. The value of x for the determination of those plasma levels is preferably changed by at least 2% more preferably at least 4%, even more preferably at least 6%, particularly at least 8%, especially at least 10%, more preferably at least 15%, most preferably at least 20% when determined under standardized conditions in terms of feeding and exercise. In one embodiment, the numbers preferably apply to a reduction.

In the context of the invention, polar lipids are defined as compounds selected from the group of phosphatidylcholines, phosphatidylethanolamines, phosphatidylserines, phosphatidylinositols, plasmalogens, either substituted with acyl- and/or alkyl moieties, glycosylated lipids, glycosylated fatty acids, sphingolipids, sphingomyelins and cholesterylesters of fatty acids. The polar lipids are preferably compounds selected from the group of phosphatidylcholines, phosphatidylethanolamines, phosphatidylserines, phosphatidylinositols, most preferably PC compounds.

In one aspect, the invention is particularly directed to a specific set of polar lipid compounds, particularly phosphatidylcholine compounds. In a preferred embodiment, the invention pertains to treating or preventing impaired plasma levels of at least one, preferably at least two, more preferably at least three polar lipid species, more preferably phosphatidylcholine species selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6]. The invention particularly relates to treating or preventing impaired plasma levels of at least one polar lipid species, more preferably at least one PC species selected from the group consisting of 36:6, 38:6 and 40:6, more preferably at least two of these polyunsaturated PC species. The invention is particularly directed to treating or preventing impaired plasma levels of at least PC aa 40:6 and/or PC ae 40:6, most preferably at least PC aa 40:6.

In another aspect, the invention is particularly directed to a specific set of polar lipids selected from the group of phosphatidylcholines, phosphatidylethanolamines, phosphatidylserines, phosphatidylinositols, plasmalogens, either substituted with acyl-and/or alkyl moieties, glycosylated lipids, glycosylated fatty acids, sphingolipids, sphingomyelins and cholesterylesters of fatty acids. The polar lipids are preferably compounds selected from the group of phosphatidylcholines, phosphatidylethanolamines, phosphatidylserines, phosphatidylinositols.

Throughout the document, when addressing the preferred plasma polar lipids targeted with the invention,
PC=phospatidylcholine;
PE=phosphatidylethanolamine;
PI=phosphatidylinositol;
PS=phosphatidylserine,
CE=cholesterol ester;
'ae' (as in aePC, aePS, aePE and aePI)=acyl-akyl;
SM=sphingomyeline;
DSM=dihydrosphingomyeline;
'l' (as in lPC, lPS, lPE and lPI)=lyso;
PA=phosphatidic acid.

By way of example, 'C16:1 CE' stands for cholesterol ester with a carbon chain with 16 C atoms and 1 double or unsaturated bond.

In one embodiment, the polar lipids are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5);

aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), for which it was found that plasma levels could be increased with the composition according to the invention, and polar lipids selected from the group consisting of C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5), for which it was found that plasma levels could be decreased with the composition according to the invention.

More preferably, the plasma polar lipids which plasma levels are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), more preferably selected from the group consisting of PC(38:0); aePC(40:6); PC(36:6); PC(38:6); and PC(40:6).

In one embodiment, the polar lipids are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), for which it was found that plasma levels could be increased with the composition according to the invention, and polar lipids selected from the group consisting of C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); LPC(20:3); PC(34:3); PC(36:3); PC(38:1); PC(38:2); PC(40:3); and PE(40:5).

Most preferably, the plasma polar lipids which are increased by the composition according to the invention are selected from the group consisting of lPC(18:0); lPC(20:5); lPC(22:6); PC(36:5); PC(38:4); PC(38:5); PE(38:6); PE(40:6); PE(40:7); aePC(38:5); aePC(38:6); and aePE(38:6) and the plasma polar lipids which plasma levels are decreased by the composition according to the invention are preferably PC(34:3) and/or PC(36:3).

In one embodiment, the polar lipids are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), for which it was found that plasma levels could be increased with the composition according to the invention, and polar lipids selected from the group consisting of C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5).

More preferably, the plasma polar lipids which plasma levels are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), Most preferably, the plasma polar lipids which are increased by the composition according to the invention are selected from the group consisting of PC(36:5); C(38:6); PC(40:6), particularly PC(36:5).

In one embodiment, the polar lipids are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), for which it was found that plasma levels could be increased with the composition according to the invention, and polar lipids selected from the group consisting of C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5), for which it was found that plasma levels could be decreased with the composition according to the invention.

More preferably, the plasma polar lipids which plasma levels are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and LPC(22:6).

Most preferably, the plasma polar lipids which are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePE(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6), particularly PC(38:4); PI(38:4); SM(24:1).

In one embodiment, the plasma polar lipids which plasma levels are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6).

More preferably, the polar lipid contains choline and/or has more than 4 double bonds, and is selected from the group consisting of aePC(36:0); aePC(38:0); aePC(38:4); aePC(40:4); LPC(18:0); LPC(18:3); LPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); and lPC(22:6).

More preferably, the polar lipid has more than 4 double bonds, and is selected from the group consisting of aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); LPC(22:6), more preferably the polar lipid has more than 5 double bonds, and is selected from the group consisting of C22:6 CE; aePC(38:6); aePC(40:6); aePE(40:6); PC(36:6); PC(38:6); PC(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC(22:6), even more preferably the polar lipid has more than 6 double bonds, and is selected from the group consisting of PC(40:7); PC(40:8); PC(42:10); PC(42:7); PC(42:8); PC(42:9); PE(40:7); and LPC(22:6), particularly lPC(22:6).

In one embodiment, the plasma polar lipids which are increased by the composition according to the invention are selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:4); PC(40:4); DSM(18:0); aePC(32:1); aePC(32:2); aePC(34:0); PC(44:2); SM(16:0); SM(18:0); SM(22:0); SM(24:0); SM(24:1); ePC(36:5); ePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePE(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC(22:6).

More preferably, the polar lipid contains choline and/or has more than 4 double bonds, and is selected from the group consisting of aePC(36:0); aePC(38:0); aePC(38:4); aePC(40:4); lPC(18:0); lPC(18:3); lPC(20:4); PC(36:1); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; ePC(38:6); ePE(40:6); PC(42:6); PI(40:6); C22:5 CE; aePE(38:6); IPE(22:6); PE(38:6); PE(40:6); PI(40:7); PC(40:8); PC(42:10); PC(42:7); PC(42:8); PC(42:9); PE(40:7); LPC(22:6).

More preferably, the polar lipid has more than 4 double bonds, and is selected from the group consisting of aePC (36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePE(40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC(22:6), even more preferably the polar lipid has more than 6 double bonds, and is selected from the group consisting of C22:6 CE; aePC(38:6); aePE (40:6); PC(42:6); PI(40:6); C22:5 CE; aePE(38:6); IPE(22:6); PE(38:6); PE(40:6); PI(38:6); PC(40:7); PC(40:8); PC(42:10); PC(42:7); PC(42:8); PC(42:9); PE(40:7); lPC (22:6), particularly lPC(22:6).

In one embodiment, the polar lipids are selected from the group consisting of C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); PE(40:5), for which it was found that plasma levels could be decreased with the composition according to the invention.

More preferably, the plasma polar lipids which are decreased by the composition according to the invention contain choline and/or more than 4 double bonds and are selected from the group consisting of aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); PE(40:5), particularly the plasma polar lipid with more than 4 double bounds PE(40:5).

In one embodiment, the plasma polar lipids have more than 3 double bonds and are selected from the group consisting of C22:5 CE; lPC(22:5); C20:4 CE; aePC(38:4); aePC(40:4); lPC(20:4); PC(38:4); PI(38:4); PC(40:4); C20:5 CE; aePC(36:5); aePC(40:5); lPC(20:5); PC(36:5); PC(36:6); PC(38:5); PI(40:5); ePC(38:5); PC(40:5); PI(38:5); PC(42:8); PC(42:6); PC(40:8); PC(42:10); PC(42:7); PC(42:9); C22:6 CE; aePC(38:6); aePC(40:6); aePE(38:6); aePE(40:6); IPE(22:6); PC(38:6); PC(40:6); PC(40:7); PE(38:6); PE(40:6); PE(40:7); PI(38:6); PI(40:6); lPC(22:6), for which it was found that plasma levels could be increased with the composition according to the invention, and polar lipids having more than 3 double bonds.

More preferably, the plasma polar lipids having more than 3 double bonds, which plasma polar lipids are increased by the composition according to the invention are selected from the group consisting of C22:5 CE; lPC(22:5); C20:4 CE; aePC(38:4); aePC(40:4); lPC(20:4); PC(38:4); PI(38:4); PC(40:4); C20:5 CE; aePC(36:5); aePC(40:5); lPC(20:5); PC(36:5); PC(38:5); PI(40:5); aePC(38:5); PC(40:5); PI(38:5); PC(42:8); PC(42:6); PC(40:8); PC(42:10); PC(42:7); PC(42:9); C22:6 CE; aePC(38:6); aePE(38:6); aePE(40:6); LPE(22:6); PC(40:7); PE(38:6); PE(40:6); PE(40:7); PI(38:6); PI(40:6); lPC(22:6).

In one embodiment, the plasma polar lipids have more than 3 double bonds, contain DHA, EPA or AA and which plasma polar lipids are increased by the composition according to the invention are selected from the group consisting of C20:4 CE; aePC(38:4); aePC(40:4); lPC(20:4); PC(38:4); PI(38:4); PC(40:4); C20:5 CE; aePC(36:5); aePC(40:5); lPC(20:5); PC(36:5); PC(36:6); PC(38:5); PI(40:5); aePC(38:5); PC(40:5); PI(38:5); PC(42:8); PC(42:6); PC(40:8); PC(42:10); PC(42:7); PC(42:9); C22:6 CE; aePC(38:6); aePC(40:6); aePE(38:6); aePE(40:6); IPE(22:6); PC(38:6); PC(40:6); PC(40:7); PE(38:6); PE(40:6); PE(40:7); PI(38:6); PI(40:6); lPC(22:6), preferably selected from the group consisting of C20:4 CE; aePC(38:4); aePC(40:4); lPC(20:4); PC(38:4); PI(38:4); PC(40:4); C20:5 CE; aePC(36:5); aePC (40:5); lPC(20:5); PC(36:5); PC(38:5); PI(40:5); aePC(38:5); PC(40:5); PI(38:5); PC(42:8); PC(42:6); PC(40:8); PC(42:10); PC(42:7); PC(42:9); C22:6 CE; aePC(38:6); aePE(38:6); aePE(40:6); LPE(22:6); PC(40:7); PE(38:6); PE(40:6); PE(40:7); PI(38:6); PI(40:6); lPC(22:6), more preferably selected from the group consisting of C20:5 CE; aePC(36:5); aePC(40:5); lPC(20:5); PC(36:5); PC(36:6); PC(38:5); PI(40:5); aePC(38:5); PC(40:5); PI(38:5); PC(42:8); PC(42:6); PC(40:8); PC(42:10); PC(42:7); PC(42:9); C22:6 CE; aePC(38:6); aePC(40:6); aePE(38:6); aePE(40:6); IPE(22:6); PC(38:6); PC(40:6); PC(40:7); PE(38:6); PE(40:6); PE(40:7); PI(38:6); PI(40:6); lPC(22:6), most preferably selected from the group consisting of C20:5 CE; aePC(36:5); aePC(40:5); lPC(20:5); PC(36:5); PC(38:5); PI(40:5); aePC(38:5); PC(40:5); PI(38:5); PC(42:8); PC(42:6); PC(40:8); PC(42:10); PC(42:7); PC(42:9); C22:6 CE; aePC(38:6); aePE(38:6); aePE(40:6); IPE(22:6); PC(40:7); PE(38:6); PE(40:6); PE(40:7); PI(38:6); PI(40:6); lPC(22:6), particularly lPC(22:6) and/or PC(40:6), especially lPC(22:6).

Alternatively, the plasma polar lipids be selected for having more than 3 double bonds, not containing DHA, and which plasma polar lipid levels are decreased by the composition according to the invention, in which case the polar lipid is preferably selected from the group consisting of the group consisting of PE(36:4); PE(38:4); PE(40:4); PS(38:4); and PE(40:5).

In one embodiment, the plasma polar lipids have more than 24 C atoms and are selected from the group consisting of aePC(32:1); aePC(32:2); aePC(34:0); PA(34:3); PI(34:1); aePC(36:5); aePC(38:0); aePC(38:4); aePC(38:6); aePE(38:6); PC(36:5); PC(36:6); PC(38:0); PC(38:4); PC(38:5); PC(38:6); PE(36:0); PE(38:0); PE(38:6); PI(38:6); aePC(36:0); aePC(38:5); PC(36:1); PI(38:2); PI(38:4); PI(38:5); aePC(40:4); aePC(40:5); aePC(40:6); aePE(40:6); PC(40:6); PC(40:7); PC(42:8); PC(44:2); PE(40:6); PE(40:7); PI(40:5); PI(40:6); PC(40:4); PC(40:5); PC(40:8); PC(42:10); PC(42:6); PC(42:7); PC(42:9), which plasma polar lipid levels are increased by the composition according to the invention, and/or the plasma polar lipid has more than 24 C atoms and is selected from the group consisting of PC(34:3); PE(34:1); PE(34:2); aePC(36:1); aePC(38:1); aePC(38:2); aePC(38:3); PC(36:3); PC(38:1); PC(38:2); PE(36:1); PE(36:2); PE(36:3); PE(36:4); PE(38:3); PE(38:4); PI(36:3); PI(38:3); PS(38:4); aePC(40:2); aePC(40:3); PC(40:3); PE(40:4); PE(40:5) which plasma polar lipid levels are increased by the composition according to the invention.

Within the above groups, the preferred plasma polar lipids are aePC(32:1); aePC(32:2); aePC(34:0); PA(34:3); PI(34:1); aePC(36:5); aePC(38:0); aePC(38:4); aePC(38:6); aePE(38:6); PC(36:5); PC(38:4); PC(38:5); PE(36:0); PE(38:0); PE(38:6); PI(38:6); aePC(36:0); aePC(38:5); PC(36:1); PI(38:2); PI(38:4); PI(38:5); aePC(40:4); aePC(40:5); aePE(40:6); PC(40:7); PC(42:8); PC(44:2); PE(40:6); PE(40:7); PI(40:5); PI(40:6); PC(40:4); PC(40:5); PC(40:8); PC(42:10); PC(42:6); PC(42:7); PC(42:9), and PC(34:3); PE(34:1); PE(34:2); aePC(36:1); aePC(38:1); aePC(38:2); aePC(38:3); PC(36:3); PC(38:1); PC(38:2); PE(36:1); PE(36:2); PE(36:3); PE(36:4); PE(38:3); PE(38:4); PI(36:3); PI(38:3); PS(38:4); aePC(40:2); aePC(40:3); PC(40:3); PE(40:4); PE(40:5).

Within the above groups, even more preferred are aePC (36:5); aePC(38:0); aePC(38:4); aePC(38:6); aePE(38:6); PC(36:5); PC(36:6); PC(38:0); PC(38:4); PC(38:5); PC(38:6); PE(36:0); PE(38:0); PE(38:6); PI(38:6); aePC(36:0);

aePC(38:5); PC(36:1); PI(38:2); PI(38:4); PI(38:5); aePC(40:4); aePC(40:5); aePC(40:6); aePE(40:6); PC(40:6); PC(40:7); PC(42:8); PC(44:2); PE(40:6); PE(40:7); PI(40:5); PI(40:6); PC(40:4); PC(40:5); PC(40:8); PC(42:10); PC(42:6); PC(42:7); PC(42:9), and aePC(36:1); aePC(38:1); aePC(38:2); aePC(38:3); PC(36:3); PC(38:1); PC(38:2); PE(36:1); PE(36:2); PE(36:3); PE(36:4); PE(38:3); PE(38:4); PI(36:3); PI(38:3); PS(38:4); aePC(40:2); aePC(40:3); PC(40:3); PE(40:4); PE(40:5)

Particularly preferred are aePC(36:5); aePC(38:0); aePC(38:4); aePC(38:6); aePE(38:6); PC(36:5); PC(38:4); PC(38:5); PE(36:0); PE(38:0); PE(38:6); PI(38:6); aePC(36:0); aePC(38:5); PC(36:1); PI(38:2); PI(38:4); PI(38:5); aePC(40:4); aePC(40:5); aePE(40:6); PC(40:7); PC(42:8); PC(44:2); PE(40:6); PE(40:7); PI(40:5); PI(40:6); PC(40:4); PC(40:5); PC(40:8); PC(42:10); PC(42:6); PC(42:7); PC(42:9), and aePC(36:1); aePC(38:1); aePC(38:2); aePC(38:3); PC(36:3); PC(38:1); PC(38:2); PE(36:1); PE(36:2); PE(36:3); PE(36:4); PE(38:3); PE(38:4); PI(36:3); PI(38:3); PS(38:4); aePC(40:2); aePC(40:3); PC(40:3); PE(40:4); PE(40:5).

Most preferred are those specific polar lipids having more than 38 C atoms, selected from the group consisting of aePC(40:4); aePC(40:5); aePC(40:6); aePE(40:6); PC(40:6); PC(40:7); PC(42:8); PC(44:2); PE(40:6); PE(40:7); PI(40:5); PI(40:6); PC(40:4); PC(40:5); PC(40:8); PC(42:10); PC(42:6); PC(42:7); PC(42:9), and aePC(40:2); aePC(40:3); PC(40:3); PE(40:4); PE(40:5) preferably aePC(40:4); aePC(40:5); aePE(40:6); PC(40:7); PC(42:8); PC(44:2); PE(40:6); PE(40:7); PI(40:5); PI(40:6).

Especially preferred are PC(40:4); PC(40:5); PC(40:8); PC(42:10); PC(42:6); PC(42:7); PC(42:9) [which plasma levels increase upon intervention with the composition of the invention] and aePC(40:2); aePC(40:3); PC(40:3); PE(40:4); PE(40:5) [which plasma levels increase upon intervention with the composition of the invention].

In one embodiment, the plasma polar lipid contains choline, and is selected from the group consisting of DSM(18:0); aePC(32:1); aePC(32:2); aePC(34:0); aePC(36:5); aePC(38:0); aePC(38:4); aePC(38:6); aePC(40:4); aePC(40:5); aePC(40:6); LPC(18:3); LPC(20:4); LPC(20:5); LPC(22:6); PC(36:5); PC(36:6); PC(38:0); PC(38:4); PC(38:5); PC(38:6); PC(40:6); PC(40:7); PC(42:8); PC(44:2); SM(16:0); SM(18:0); SM(22:0); SM(24:0); SM(24:1); aePC(36:0); aePC(38:5); LPC(18:0); LPC(22:5); PC(36:1); PC(40:4); PC(40:5); PC(40:8); PC(42:10); PC(42:6); PC(42:7); PC(42:9) preferably DSM(18:0); aePC(32:1); aePC(32:2); aePC(34:0); aePC(36:5); aePC(38:0); aePC(38:4); aePC(38:6); aePC(40:4); aePC(40:5); LPC(18:3); LPC(20:4); LPC(20:5); LPC(22:6); PC(36:5); PC(38:4); PC(38:5); PC(40:7); PC(42:8); PC(44:2); SM(16:0); SM(18:0); SM(22:0); SM(24:0); SM(24:1); aePC(36:0); aePC(38:5); LPC(18:0); LPC(22:5); PC(36:1); PC(40:4); PC(40:5); PC(40:8); PC(42:10); PC(42:6); PC(42:7); PC(42:9). The plasma levels of these choline-containing polar lipids increase upon intervention with the composition of the invention.

In one aspect, the most preferred plasma polar lipids are lPC 22:6 and/or PC 40:6, preferably at least lPC 22:6.

In the method or use according to the invention, the B vitamins are administered in therapeutically effective amounts to improve the plasma polar lipid levels.

Subject

In particular, the subject is a human being that suffers from impaired plasma concentrations of at least one of the above species, which subject is at increased risk of developing preclinical AD or MCI, or is a preclinical AD or MCI subject.

The subject could be an adult, preferably elderly, not diagnosed with any cognitive or neurological disorder, which is preferably a subject in need of an increase in the plasma concentration of the specific polar lipids mentioned here above. The subject in need thereof is preferably defined as a subject of at least 50 years of age, male and/or female, the subject having a disturbed plasma polar lipid profile as defined earlier in the text. The subject can have preclinical MCI and/or AD, or the subject can have a diagnosis of MCI and/or AD.

In one embodiment, a subject that may be targeted with the composition of the invention suffers from impaired plasma polar lipids concentrations preferably impaired plasma phosphatidylcholine concentrations compared to a control subject, preferably exhibiting plasma levels of at least 1, preferably at least 2, more preferably at least 3 of said polar lipid species, preferably phosphatidylcholine species as defined above which are significantly changed, preferably with at least 2% more preferably at least 4%, even more preferably at least 6%, particularly at least 8%, especially at least 10%, more preferably at least 15%, most preferably at least 20%. The plasma phospholipids involve the specific polar lipid species, preferably phosphatidylcholine species selected from the group consisting of PC aa C36:6, PC aa C38:0, PC aa C38:6, PC aa C40:6 and PC ae C40:6, more preferably one or more PC species selected from the group consisting of PC aa C36:6, PC aa C38:6, PC aa C40:6 and PC ae C40:6, most preferably one or more PC species selected from the group consisting of PC aa C40:6 and PC ae C40:6, most preferably at least PC aa 40:6.

In one embodiment, the polar lipid, preferably phosphatidylcholine, has a glycerol portion and the glycerol portion is bonded to two fatty acids. The amount of carbons in the fatty acids is preferably about 16 to 40 carbon atoms, preferably 16, 36, 38 or 40 carbon atoms, most preferably at least 36 carbon atoms. The fatty acids preferably have about 0-6 double bonds, preferably 1-6 double bonds, more preferably at 2 double bonds.

The subject is preferably a human, preferably an elderly human being, 'elderly' meaning preferably at least 50 years of age. Preferably the elderly subject has no cognitive deficits.

In one embodiment, the subject is preferably a drug-naïve subject, which subject has preferably not been administered any drug for memory improvement and or for AD at least 4 weeks prior to the administration of a composition according to the invention. Preferably, the term 'drug naïve' as used in the present invention refers to subjects who do not ingest one or more of cholinesterase inhibitors, N-methyl-D-aspartate (NMDA) antagonists and ginkgo biloba during treatment with the composition of the invention, and preferably have not taken any cognitive ability-affecting drugs in the 4 weeks prior to the treatment.

Product

Throughout the application, the terms 'product' and 'composition' are used interchangeably and account for the combination of ingredients administered to a subject in need thereof.

In one aspect of the present invention, the composition according to the invention may be used as a pharmaceutical product comprising one or more pharmaceutically acceptable carrier materials. In another, preferred aspect of the present invention, the composition according to the invention may be used as a nutritional product, for example as a nutritional supplement, e.g., as an additive to a normal diet, as a fortifier, to add to a normal diet, or as a complete nutrition.

The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavoring agents, preservatives, stabilizers, emulsifying agents, buffers and the like may be added in accordance with accepted practices of pharmaceutical compounding. While the individual active ingredients are suitably administered in a single composition, they may also be administered in individual dosage units. If the composition is a pharmaceutical product, such product may contain the daily dosage in one or more dosage units. The dosage unit may be in a liquid form or in a solid form, wherein in the latter case the daily dosage may be provided by one or more solid dosage units, e.g. in one or more capsules or tablets.

In another aspect of the present invention, the composition according to the invention may be used in a nutritional product comprising at least one component selected from the group of fats, proteins, and carbohydrates. It is understood that a nutritional product differs from a pharmaceutical product by the presence of nutrients which provide nutrition to the subject to which the composition is administered, in particular the presence of protein, fat, digestible carbohydrates and dietary fibers. It may further contain ingredients such as minerals, vitamins, organic acids, and flavoring agents. Although the term "nutraceutical product" is often used in literature, it denotes a nutritional product with a pharmaceutical component or pharmaceutical purpose. Hence, the nutritional composition according to the invention may also be used in a nutraceutical product.

The product according to the invention comprises at least one B complex vitamin, preferably a B vitamin selected from the group consisting of vitamin B6 (pyridoxine, pyridoxal, or pyridoxamine, or pyridoxine hydrochloride), vitamin B9 (folic acid or folate), and vitamin B12 (various cobalamins). Throughout the application, functional equivalents are encompassed within these terms.

Preferably the present composition comprises at least two selected from the group consisting of vitamin B6, vitamin B12 and vitamin B9. In particular, good results have been achieved with a combination comprising vitamin B6 and vitamin B9. In one embodiment, the composition comprises vitamins B6, B9 and B12. Again, functional equivalents are encompassed within these terms.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (IOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose preferably does not exceed the tolerable upper intake levels (UL), as recommended by IOM.

If present in the nutritional composition or medicament, the vitamin B6 is preferably present in an amount to provide a daily dosage in the range of 0.5 to 100 mg, in particular in the range of 0.7 to 20 mg, more in particular in the range of 0.8 to 10 mg. The present composition preferably comprises 0.5 to 100 mg vitamin B6 per 100 g (liquid) product, more preferably 0.7 to 20 mg vitamin B6 per 100 g (liquid) product, more preferably 0.8 to 10 mg vitamin B6 per 100 g (liquid) product.

If present in the nutritional composition or medicament, the vitamin B12 is preferably present in an amount to provide a daily dosage in the range of 0.5 to 10000 µg, more preferably 0.5 to 1000 µg, in particular in the range of 0.8 to 500 µg, more in particular in the range of 1 to 5 µg. The present composition preferably comprises 0.5-10000 µg, more preferably 0.5-1000 µg vitamin B12 per 100 g (liquid) product, more preferably 0.8 to 500 µg vitamin B12 per 100 g (liquid) product, more preferably 1 to 5 µg vitamin B12 per 100 g (liquid) product. The term "vitamin B12" incorporates all cobalbumin equivalents known in the art.

Throughout the application, the terms 'folic acid', 'folate' and 'B9' are used interchangeably. If present in the nutritional composition or medicament, the vitamin B9 is preferably present in an amount to provide a daily dosage in the range of 100 to 5000 µg, in particular in the range of 150 to 1000 µg, more in particular in the range of 200 to 600 µg. The present composition preferably comprises 100 to 5000 µg folic acid per 100 g (liquid) product, more preferably 150 to 1000 µg folic acid per 100 g (liquid) product, more preferably 200 to 600 µg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

The product of the invention is an enteral composition, intended for oral administration. It is preferably administered in liquid form. In one embodiment, the product comprises a lipid fraction and at least one of carbohydrates and proteins, wherein the lipid composition provides between 20 and 50 energy % of the food product. In one embodiment, the food product is a liquid composition containing between 0.8 and 1.4 kcal per ml.

Preferably, the composition comprising B vitamin(s) further comprises an uridine source.

Uridine, UMP

The present composition preferably comprises uridine, cytidine and/or an equivalent thereof, including salts, phosphates, acyl derivatives and/or esters. In terms of uridine, the composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied. Preferably, the composition to be administered according to the present invention comprises a source of uridine selected from the group consisting of uridine, deoxyuridine, uridine phosphates, uracil, and acylated uridine, and cytidine, more preferably selected from the group consisting of uridine, deoxyuridine, uridine phosphates, uracil, and acylated uridine.

Preferably, the present composition comprises an uridine phosphate selected from the group consisting of uridine monophosphate (UMP), uridine diphosphate (UDP) and uridine triphosphate (UTP); and/or a cytidine phosphate (CMP, CDP, CTP, preferably CMP). Most preferably the present composition comprises UMP, as UMP is most efficiently being taken up by the body. Preferably at least 50 weight % of the uridine in the present composition is provided by UMP, more preferably at least 75 weight %, most preferably at least 95 weight %. Doses that must be administered are given as UMP. The amount of uracil sources can be calculated taking the molar equivalent to the UMP amount (molecular weight 324 Dalton).

The present method preferably comprises the administration of uridine (the cumulative amount of uridine, deoxyuridine, uridine phosphates, nucleobase uracil and acylated uridine derivatives) in an amount of in an amount of 0.08-3 g per day, preferably 0.1-2 g per day, more preferably 0.2-1 g per day. The present method preferably comprises the administration of a composition comprising uridine in an amount of 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day. The above amounts also account for any amounts of cytidine, cytidine phosphates and citicoline incorporated in the composition or method.

Preferably, the present composition comprises uridine phosphate, preferably uridine monophosphate (UMP). The UMP is very efficiently taken up by the body. Hence, inclusion of UMP in the present composition enables a high effectivity at the lowest dosage and/or the administration of a low volume to the subject.

Choline

In a preferred embodiment, the present composition contains choline, a choline salt and/or choline ester. For the remainder of the paragraph, the term 'choline' shall be considered to encompass all these equivalents. The choline salt is preferably selected from choline chloride, choline bitartrate, or choline stearate. The choline ester is preferably selected from a phosphatidylcholine and lyso-phosphatidylcholine. The present method preferably comprises the administration of more than 50 mg choline per day, preferably 80 to 2000 mg choline per day, more preferably 120 to 1000 mg choline per day, most preferably 150 to 600 mg choline per day. The present composition preferably comprises 50 mg to 3000 gram choline per 100 ml of the liquid composition, preferably 200 mg to 1000 mg choline per 100 ml. The above numbers are based on choline, the amounts of choline equivalents or sources can be calculated taking the molar equivalent to choline into account.

DHA/EPA

In one embodiment, the composition preferably further comprises, in addition to the B vitamin component(s) and the preferred uridine compound(s), a lipid fraction comprising at least one of docosahexaenoic acid (22:6; DHA), eicosapentaenoic acid (20:5; EPA) and docosapentaenoic acid (22:5; DPA), or esters thereof. In the context of the invention, 'DPA' is understood to comprise the omega-3 (22:5) DPA only.

The composition preferably comprises at least one ω-3 polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA.

Preferably the present composition contains at least DHA, more preferably DHA and EPA. EPA is converted to DPA (ω-3), increasing subsequent conversion of DPA to DHA in the brain. Hence, the present composition preferably contains a significant amount of EPA, so to further stimulate in vivo DHA formation.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 400 to 5000 mg DHA+EPA+DPA (preferably DHA+EPA) per day, more preferably 500 to 3000 mg (preferably DHA+EPA) per day, most preferably 1000 to 2500 mg (preferably DHA+EPA) per day. DHA is preferably administered in an amount of 300 to 4000 mg per day, more preferably 500 to 2500 mg per day.

The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10wt. % EPA based on total fatty acids. The above-mentioned amounts take into account and optimize several aspects, including taste (e.g. too high LCP levels reduce taste, resulting in a reduced compliance).

The present composition preferably contains at least one oil selected from fish oil, algae oil and eggs lipids. Preferably the present composition contains fish oil comprising DHA and EPA.

The ratio of the weights of DHA to EPA is preferably larger than 1, more preferably 2:1 to 10:1, more preferably 3:1 to 8:1. The above-mentioned ratios and amounts take into account and optimize several aspects, including taste (too high LCP levels reduce taste, resulting in a reduced compliance), balance between DHA and precursors thereof to ensure optimal effectiveness while maintaining low-volume formulations.

Sources of DHA possible sources of DHA: tuna oil, (other) fish oils, DHA rich alkyl esters, algae oil, egg yolk, or phospholipids enriched with n-3 LCPUFA e.g. phosphatidylserine-DHA.

The present composition preferably contains a very low amount of arachidonic acid (AA). Preferably the weight ratio DHA/AA in the present composition is at least 5, preferably at least 10, more preferably at least 15, preferably up to e.g. 30 or even up to 60. The present method preferably comprises the administration of a composition comprising less than 5 wt. % arachidonic acid based on total fatty acids, more preferably below 2.5 wt. % , e.g. down to 0.5 wt %.

The weight ratio omega-6/omega-3 fatty acids in the present product is preferably below 0.5, more preferably below 0.2, e.g. down to 0.05 or to 0.01. The ratio ω-6/ω-3 fatty acids (C 20 and higher) in the present product is preferably below 0.3, more preferably below 0.15, e.g. down to 0.06 or to 0.03.

Saturated and Monounsaturated Fatty Acids

The present composition preferably comprises saturated and/or mono-unsaturated fatty acids. The amount of saturated fatty acids is preferably 6-60 wt. % based on total fatty acids, preferably 12-40 wt. % , more preferably 20-40 wt. % based on total fatty acids. In particular the amount of C14:0 (myristic acid) +C16:0 (palmitic acid) is preferably 5-50 wt. % , preferably 8-36 wt. % , more preferably 15-30 wt. % , based on total fatty acids. The total amount of monounsaturated fatty acids, such as oleic acid and palmitoleic acid, is preferably between 5 and 40 wt. % , more preferably between 15 and 30 wt. % . A composition with these preferred amounts was found to be very effective.

Phospholipids

Preferably, the present composition preferably comprises phospholipids, preferably 0.1-50 wt. % phospholipids based on total weight of lipids, more preferably 0.5-20 wt. % , more preferably between 1 and 10% wt. % , most preferably between 1 and 5 wt. % based on total weight of lipids. The total amount of lipids is preferably between 10 and 30 wt. % on dry matter, and/or between 2 and 10 g lipid per 100 ml for a liquid composition. The composition preferably comprises between 0.01 and 1 gram lecithin per 100 ml, more preferably between 0.05 and 0.5 gram lecithin per 100 ml. A composition with these preferred amounts was found to be very effective. In one embodiment, the phospholipids comprise at least two phospholipids selected from the group consisting of phosphatidylcholine, phosphatidylethanolamine, phosphatidylinositol and phosphatidylserine, preferably at least PC and PE. In a preferred embodiment, the phospholipids optionally present in the composition contain insignificant amounts (i.e at most in trace amounts, preferably below detection limits) of any of the above-identified PCs.

Vitamins C, E

Vitamin C, or a functional equivalent thereof, may be present in an amount to provide a daily dosage in the range of 20 to 2000 mg, in particular in the range of 30 to 500 mg, more in particular in the range of 75 to150 mg. In one embodiment, vitamin C, or a functional equivalent thereof, is present in an amount in the range of 20 to 2000 mg, in particular in the range of 30 to 500 mg, more in particular in the range of 75 to150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to100 mg, to prevent oxidative damage resulting from dietary PUFA. In one embodiment, tocopherol and/or equivalent is present in an amount in the range of 10 to 300 mg, in particular in the range of 30 to 200 mg, more in particular in the range of 35 to100 mg per 100 ml of the composition. The term "tocopherol and/or an equivalent thereof", and 'alpha-TE', as used in this description, comprises tocopherols, tocotrienols, pharmaceutical and/or nutritional acceptable derivatives thereof and any combination thereof. The above numbers are based on tocopherol equivalents, recognized in the art.

Selenium

The present composition preferably contains selenium, because of its antioxidant activity. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

Protein

Although the composition may further comprise proteinaceous material, it has been found that such component is not deemed necessary. In fact, it is thus possible to concentrate the actives in a low volume composition. Should a protein fraction be included, the protein fraction comprises intact proteins, peptides as may be obtained by hydrolyses of intact proteins and by syntheses, derivatives of peptides comprising more than 80 weight % amino acids. Nitrogen from nucleosides material and choline will not be calculated as being protein.

In one embodiment, it is preferred that the amount of taurine (including taurine salts) is less than 0.1 g, preferably less than 0.05 g per daily dose. Additionally or alternatively, it is preferred that the amount of taurine (including taurine salts) is less than 5 mg, more preferably less than 2.5 g per 100 g composition.

In one embodiment, the composition comprises less than 25 mg, more preferably less than 20 mg, most preferably less than 15 mg cysteine and taurine per 100 ml of the (liquid) composition. In one embodiment, the composition comprises less than 25 mg, more preferably less than 20 mg, most preferably less than 15 mg cysteine per 100 ml of the (liquid) composition. It is preferred that the protein fraction comprises more than 70 weight % of casein or caseinates, or hydrolyzates thereof, and more preferably 80 weight % or more, because caseins comprise relatively low amounts of cysteine compared to other protein sources. It is further preferred to heat the liquid composition in order to oxidize the cysteine molecules present in the protein. This impairs biological availability of any residual cysteine as present in the formula. A preferred heat treatment involves sterilization. It is preferred to maintain the temperature remains below 135° C., preferably less than 132° C. combined with a sufficient long time to have the cysteine oxidized, i.e. more than 30 seconds, preferably more than 40 seconds.

In one embodiment, it is preferred that the composition has a protein content of less than 15 en %, more preferably less than 10 en %, most preferably less than 5 en % of the total energy content of the composition. The energy percentages of the components are calculated using the calculation factors 9 kcal per g lipid, 4 kcal per g protein or g digestible carbohydrates, 2 kcal per g dietary fibers and zero kcal for the other components in the composition. In one embodiment, it is preferred that the composition comprises less than 0.5 to 10 g protein per 100 ml, more preferably less than 1 to 6 gram protein per 100 ml, most preferably 2 to 6 gram protein/100 ml.

Preferably the composition comprising B vitamin(s) further comprises one or more of DHA, EPA, a uridine source (preferably UMP), phospholipids, choline, vitamin E, vitamin C, selenium. More preferably the composition comprises vitamin B12, vitamin B6 and folic acid, a uridine source (preferably UMP), and more preferably also DHA, EPA, phospholipids, choline, vitamin E, vitamin C, selenium.

A preferred composition according to the invention comprises, per daily dose or per 100 ml composition:
  0.5-10000 µg, preferably 0.5-1000 µg vitamin B12,
  0.5-100 mg, preferably 0.7-20 mg vitamin B6,
  100-5000 µg, preferably 150-1000 µg folic acid,
  100-500 mg, preferably 200-400 mg EPA,
  900-1500 mg, preferably 950-1300 mg DHA,
  50-600 mg, preferably 60-200 mg phospholipids,
  200-600 mg, preferably 300-500 mg choline,
  400-800 mg, preferably 500-700 mg UMP (uridine monophosphate),
  20-60 mg, preferably 30-50 mg vitamin E (alpha-TE),
  60-100 mg, preferably 60-90 mg vitamin C, and
  40-80 µg, preferably 45-65 µg selenium.

More preferred, a composition according to the invention comprises per 100 ml composition:
  0.5-10000 µg, preferably 0.5-1000 µg vitamin B12,
  0.5-100 mg, preferably 0.7-20 mg vitamin B6,
  100-5000 µg, preferably 150-1000 µg folic acid,
  100-500 mg, preferably 200-400 mg EPA,
  900-1500 mg, preferably 950-1300 mg DHA,
  50-600 mg, preferably 60-200 mg phospholipids,
  200-600 mg, preferably 300-500 mg choline,
  400-800 mg, preferably 500-700 mg UMP (uridine monophosphate),
  20-60 mg, preferably 30-50 mg vitamin E (alpha-TE),
  60-100 mg, preferably 60-90 mg vitamin C, and
  40-80 µg, preferably 45-65 µg selenium.

The compositions as described above can be used as a nutritional therapy, nutritional support, as a medical food, as a food for special medical purposes or as a nutritional supplement. Such product can be consumed at one, two or three servings between 75 and 200 ml per day or per unit, most preferably between 90 and 150 ml/day, most preferably about 125 mL per day in the aforementioned applications.

The subjects that can benefit from the method and composition of the invention often experience problems with eating. Their sensory capabilities and/or control of muscles can become imparted, as well as in some instances their ambition to apply proper eating habits. Swallowing and/or mastication may be problematic. Hence, the present composition is preferably provided in the form of a drink capable of being ingested through a straw.

Related therewith, the composition according to the invention preferably has a low viscosity, preferably a viscosity between 1 and 2000 mPa·s measured at a shear rate of 100 sec-1 at 20° C., more preferably a viscosity between 1 and 100 mPa·s measured at a shear rate of 100 sec-1 at 20° C. In a preferred embodiment the present composition has a viscosity of 1-80 mPa·s at a shear rate of 100 per sec at 20° C., more preferably of 1-40 mPa·s at a shear rate of 100 per sec at 20° C. These viscosity measurements may for instance be performed using plate and cone geometry.

To be optimally accepted by the subject, the present composition preferably has an osmolality of 300 to 800 mOsm/kg. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/ml.

In one aspect, the invention pertains to a method for preventing or treating impaired plasma polar lipid levels, preferably phospholipid levels in a preclinical AD or MCI subject or a subject with a high likelihood of developing AD or MCI, comprising:
  a) analyzing plasma levels of at least one phospholipid in a subject;
  b) selecting a subject having an impaired plasma phospholipid level, preferably an impaired plasma polar lipid level, preferably impaired plasma phosphatidylcholine level, preferably an impaired plasma level of one or more PC species selected from the group consisting of phosphatidylcholine diacyl C36:6 [PC aa C36:6], PC aa C38:0, PC aa C38:6, PC aa C40:6 and PC acyl-alkyl C40:6 [PC ae C40:6];
  c) administering to said selected subject a composition comprising at least one, preferably at least two, most preferably all B vitamins selected from the group consisting of vitamin B6, vitamin B12 and vitamin B9, and optionally one or more of uridine and cytidine, or salts, phosphates, acyl derivatives or esters thereof.

In a further aspect, the invention pertains to a composition for use in preventing or treating impaired plasma polar lipid levels, preferably phospholipid levels, more preferably plasma levels of one or more of the aforementioned polar lipid species, more preferably of one or more of the aforementioned PC species in a preclinical AD or MCI subject or a subject with a high likelihood of developing AD or MCI, wherein said subject is administered with a composition comprising at least one, preferably at least two, most preferably all B vitamins selected from the group consisting of vitamin B6, vitamin B12 and vitamin B9.

EXAMPLES

Example 1a

Liquid Product Containing Per 125 ml Serving

| | |
|---|---|
| Fat, g 4.9 | Vitamin E (alpha-TE), mg 40 |
| EPA, mg 300 | Vitamin C, mg 80 |
| DHA, mg 1200 | Selenium, µg 60 |
| Phospholipids, mg 106* | Vitamin B12, µg 3 |
| Choline, mg 400 | Vitamin B6, mg 1 |
| UMP (uridine monophosphate), mg 625 | Folic acid, µg 400 |

Abbreviations: EPA, eicosapentaenoic acid; DHA, docosahexaenoic acid; TE, tocopherol equivalents;
*Source: Lecithin. Does not contain significant amount of phosphatidylcholine diacyl C36:6 [PC aa C36:6], PC aa C38:0, PC aa C38:6, PC aa C40:6 and PC acyl-alkyl C40:6 [PC ae C40:6]

Example 1b

Liquid Product Containing Per 125 ml Serving

| | |
|---|---|
| Energy, kcal 125 | Calcium, mg 100 |
| Protein, g 3.8 | Phosphorus, mg 87.5 |
| Carbohydrate, g 16.5 | Magnesium, mg 25.0 |
| Fat, g 4.9 | Iron, mg 2 |
| EPA, mg 300 | Zinc, mg 1.5 |
| DHA, mg 1200 | Iodine, µg 16.3 |
| Phospholipids, mg 106* | Manganese, mg 0.41 |
| Choline, mg 400 | Copper, µg 225 |
| UMP (uridine monophosphate), mg 625 | Molybdenum, µg 12.5 |
| Vitamin E (alpha-TE), mg 40 | Chromium, µg 8.4 |
| Vitamin C, mg 80 | Vitamin A, µg 200 |
| Selenium, µg 60 | Thiamin (B1), mg 0.19 |
| Vitamin B12, µg 3 | Riboflavin (B2), mg 0.20 |
| Vitamin B6, mg 1 | Niacin (B3), mg NE 2.25 |
| Folic acid, µg 400 | Pantothenic acid (B5), mg 0.66 |
| Sodium, mg 125 | Vitamin D, µg 0.88 |
| Potassium, mg 187.5 | Biotin, µg 5.0 |
| Chloride, mg 156.3 | Vitamin K, µg 6.6 |

Abbreviations: EPA, eicosapentaenoic acid; DHA, docosahexaenoic acid; TE, tocopherol equivalents; NE, niacin equivalents.
*Source: lecithin. Does not contain significant amounts of phosphatidylcholine diacyl C36:6 [PC aa C36:6], PC aa C38:0, PC aa C38:6, PC aa C40:6 and PC acyl-alkyl C40:6 [PC ae C40:6]

Example 2

Combined Dietary Folate, Vitamin B12, and Vitamin B6 Intake Increases Plasma Levels of Specific Polar Lipid Species Methods
Animals A total of 24 male Sprague-Dawley rats (Crl:CD(SD)) were obtained from Charles River, Sulzfeld, Germany. Animals aged 6-8 weeks on arrival were housed in groups in a temperature- and light-controlled room, under 12 h light-12 h dark cycles. Rats had free access to food and water. Body weight was registered once a week. All animal experimental protocols were conducted in accordance with international and national laws and institutional guidelines and approved by the local ethics committee, i.e. DEC Consult, Bilthoven, The Netherlands.

Diets

Two different diets with increasing folate, vitamin B12, and vitamin B6 contents were used: 1) Bvitamin-poor; and 2) Bvitamin-normal. Diets were AIN-93 M based [1], isoenergetic, and identical with respect to their protein, carbohydrate, fat, fiber, and mineral contents. All diets were devoid of any measurable amounts of DHA. The vitamin mix (AIN-93-VX) [1] was prepared without folic acid, cyanocobalamin, and pyridoxine; these vitamins were subsequently supplemented accordingly. Diets were formulated with vitamin-free, ethanol-precipitated casein (Harlan Teklad, Madison, Wis., USA) and were manufactured by Ssniff Spezialdiäten, Soest, Germany.

The Bvitamin-poor diet contained low amounts of folate (<0.1 mg/kg), vitamin B12 (<1.0 µg/kg), and vitamin B6 (<0.6 mg/kg). No sulfathiazole drugs were added to the diet and therefore a limited amount of folate was still expected to be provided by the gut flora. Vitamin B12 deficiency in the rat is difficult to achieve because of considerable endogenous storage of this vitamin. To attain a moderate reduction of endogenous vitamin B12, the Bvitamin-poor was supplemented with 50 g/kg pectin (polygalacturonic acid, high methoxyl, Obipekting®, NF/USP Citrus; TEFCO FoodIngredients, Bodegraven, The Netherlands), which binds vitamin B12 in the intestine, making it less bioavailable [2]. Pectin consequently promotes depletion of endogenous vitamin B12 through the enterohepatic circulation the vitamin. Since pectin could affect food intake [3], the two diets were supplemented with pectin to maintain uniform intakes of the diets. Pectin has minimal effects on vitamin B12 status when the diet contains adequate amounts of this vitamin [2].

The vitamin B-normal diet provided 100% of the requirements for each of the three vitamins according to the National Research Council report on the nutrient requirements of laboratory animals [4]. The exact dietary levels of the three Bvitamins in each experimental diet are indicated in Table 1.

TABLE 1

Folate, vitamin B12, and vitamin B6 content of the experimental diets

| | | Calculated dietary levels | | |
|---|---|---|---|---|
| Diet description | % of recommended levels [4] | Folate (folic acid) | Vitamin B12 (cyanocobalamin) mg/kg diet | Vitamin B6 (pyridoxine-HCL) |
| B vitamin: poor | ~0% | <0.1 | <0.001 | <0.6 |
| B vitamin: normal | 100% | 1.0 | 0.05 | 6.0 |

Experimental Design

Animals were randomized into the two experimental groups according to their body weights at the start of the intervention period. Subsequently, rats were fed one of the two experimental diets for 4 weeks.

Tissue Preparation

After the supplementation period, animals that had been feed-deprived for 3-4 hours were killed by inhalation of isoflurane vaporized in medicinal air and subsequent decapitation by guillotine. Trunk blood was collected through a funnel into EDTA-containing tubes. After centrifugation at 1750×g for 10 min, plasma was aspirated for subsequent analyses.

Plasma Polar Lipid Species

Plasma samples were analyzed for lipid profiles at the Kansas Lipidomics Research Center using electrospray ionization tandem mass spectrometry (ESI-MS/MS).

Results

TABLE 2

Plasma concentrations of specific polar lipid species (µM)

| Parameter | B vitamin poor | B vitamin normal |
|---|---|---|
| C20:4 CE | 3150.15 | 4379.83 |
| C22:6 CE | 59.62 | 85.53 |
| ePC(36:5) | 2.72 | 3.34 |
| ePC(38:0) | 2.12 | 3.39 |
| ePC(38:6) | 2.57 | 3.19 |
| ePC(40:5) | 2.08 | 2.61 |
| ePC(40:6) | 2.29 | 2.82 |
| ePE(40:6) | 0.65 | 0.68 |
| LPC(20:5) | 0.78 | 1.18 |
| LPC(22:6) | 10.15 | 13.40 |
| PC(36:5) | 14.15 | 20.45 |
| PC(36:6) | 1.08 | 1.51 |
| PC(38:0) | 1.32 | 1.68 |
| PC(38:5) | 108.78 | 167.22 |
| PC(38:6) | 82.80 | 108.05 |
| PC(40:6) | 42.26 | 61.08 |
| PC(40:7) | 10.18 | 15.93 |
| PI(40:5) | 2.90 | 3.89 |
| PI(40:6) | 2.75 | 3.48 |
| C18:3 CE | 33.48 | 73.39 |
| ePC(38:4) | 12.10 | 15.18 |
| ePC(40:4) | 3.96 | 5.09 |
| LPC(18:3) | 1.55 | 2.22 |
| LPC(20:4) | 121.37 | 166.64 |
| PC(38:4) | 338.00 | 497.76 |
| PC(42:8) | 1.05 | 1.51 |
| C16:1 CE | 113.17 | 232.96 |
| ePC(36:0) | 0.43 | 0.51 |
| ePC(38:5) | 7.79 | 9.50 |
| LPC(18:0) | 122.02 | 150.90 |
| LPC(22:5) | 3.60 | 4.64 |
| PC(36:1) | 26.42 | 35.94 |
| PC(40:4) | 4.92 | 6.75 |
| PC(40:5) | 18.06 | 24.29 |
| PC(40:8) | 7.99 | 13.63 |
| PC(42:10) | 1.06 | 1.91 |
| PC(42:6) | 0.76 | 1.01 |
| PC(42:7) | 0.87 | 1.23 |
| PC(42:9) | 0.88 | 1.29 |
| PI(34:1) | 0.96 | 2.02 |
| PI(38:4) | 77.68 | 94.58 |
| PI(38:5) | 4.50 | 6.23 |

The plasma concentrations of these specific polar lipid species monitored could be increased significantly using increased amounts of B vitamins.

Example 3

Combined Dietary Folate, Vitamin B12, and Vitamin B6 Intake Increases Plasma Levels of Specific Polar Lipid Species Methods Animals A total of 24 male Sprague-Dawley rats (Crl:CD(SD)) were obtained from Charles River, Sulzfeld, Germany. Animals aged 6-8 weeks on arrival were housed in groups in a temperature- and light-controlled room, under 12 h light-12 h dark cycles. Rats had free access to food and water. Body weight was registered once a week. All animal experimental protocols were conducted in accordance with international and national laws and institutional guidelines and approved by the local ethics committee, i.e. DEC Consult, Bilthoven, The Netherlands.

Diets

Two different diets with increasing folate, vitamin B12, and vitamin B6 contents were used: 1) Bvitamin-poor and 2) Bvitamin-enriched. Diets were AIN-93 M based [1], isoenergetic, and identical with respect to their protein, carbohydrate, fat, fiber, and mineral contents. All diets were devoid of any measurable amounts of DHA. The vitamin mix (AIN-93-VX) [1] was prepared without folic acid, cyanocobalamin, and pyridoxine; these vitamins were subsequently supplemented accordingly. Diets were formulated with vitamin-free, ethanol-precipitated casein (Harlan Teklad, Madison, Wis., USA) and were manufactured by Ssniff Spezialdiäten, Soest, Germany.

The Bvitamin-poor diet contained low amounts of folate (<0.1 mg/kg), vitamin B12 (<1.0 μg/kg), and vitamin B6 (<0.6 mg/kg). No sulfathiazole drugs were added to the diet and therefore a limited amount of folate was still expected to be provided by the gut flora. Vitamin B12 deficiency in the rat is difficult to achieve because of considerable endogenous storage of this vitamin. To attain a moderate reduction of endogenous vitamin B12, the Bvitamin-poor was supplemented with 50 g/kg pectin (polygalacturonic acid, high methoxyl, Obipekting®, NF/USP Citrus; TEFCO FoodIngredients, Bodegraven, The Netherlands), which binds vitamin B12 in the intestine, making it less bioavailable [2]. Pectin consequently promotes depletion of endogenous vitamin B12 through the enterohepatic circulation the vitamin. Since pectin could affect food intake [3], all two diets were supplemented with pectin to maintain uniform intakes of the diets. Pectin has minimal effects on vitamin B12 status when the diet contains adequate amounts of this vitamin [2].

The vitamin B-enriched diet provided 400% of the requirements for each of the three vitamins according to the National Research Council report on the nutrient requirements of laboratory animals [4]. The exact dietary levels of the three Bvitamins in each experimental diet are indicated in Table 1.

TABLE 3

Folate, vitamin B12, and vitamin B6 content of the experimental diets

| Diet description | % of recommended levels [4] | Calculated dietary levels | | |
|---|---|---|---|---|
| | | Folate (folic acid) | Vitamin B12 (cyanocobalamin) mg/kg diet | Vitamin B6 (pyridoxine-HCL) |
| B vitamin: poor | ~0% | <0.1 | <0.001 | <0.6 |
| B vitamin: enriched | 400% | 4.0 | 0.20 | 24.0 |

Experimental Design

Animals were randomized into the two experimental groups according to their body weights at the start of the intervention period. Subsequently, rats were fed one of the two experimental diets for 4 weeks.

Tissue Preparation

After the supplementation period, animals that had been feed-deprived for 3-4 hours were killed by inhalation of isoflurane vaporized in medicinal air and subsequent decapitation by guillotine. Trunk blood was collected through a funnel into EDTA-containing tubes. After centrifugation at 1750×g for 10 min, plasma was aspirated for subsequent analyses.

Plasma Polar Lipid Species

Plasma samples were analyzed for lipid profiles at the Kansas Lipidomics Research Center using electrospray ionization tandem mass spectrometry (ESI-MS/MS).

Results

TABLE 4

Plasma concentrations of specific polar lipid species (μM)

| Parameter | B vitamin poor | B vitamin enriched |
|---|---|---|
| C20:4 CE | 3150.15 | 4826.03 |
| C22:6 CE | 59.62 | 108.71 |
| ePC(36:5) | 2.72 | 3.38 |
| ePC(38:0) | 2.12 | 3.29 |
| ePC(38:6) | 2.57 | 3.63 |
| ePC(40:5) | 2.08 | 2.91 |
| ePC(40:6) | 2.29 | 3.09 |
| ePE(40:6) | 0.65 | 0.74 |
| LPC(20:5) | 0.78 | 0.95 |
| LPC(22:6) | 10.15 | 14.46 |
| PC(36:5) | 14.15 | 18.46 |
| PC(36:6) | 1.08 | 1.60 |
| PC(38:0) | 1.32 | 1.77 |
| PC(38:5) | 108.78 | 166.63 |
| PC(38:6) | 82.80 | 115.60 |
| PC(40:6) | 42.26 | 63.91 |
| PC(40:7) | 10.18 | 16.91 |
| PI(40:5) | 2.90 | 4.41 |
| PI(40:6) | 2.75 | 4.46 |
| C18:3 CE | 33.48 | 58.44 |
| ePC(38:4) | 12.10 | 15.95 |
| ePC(40:4) | 3.96 | 5.22 |
| LPC(18:3) | 1.55 | 1.91 |
| LPC(20:4) | 121.37 | 162.49 |
| PC(38:4) | 338.00 | 490.03 |
| PC(42:8) | 1.05 | 1.63 |
| C16:1 CE | 113.17 | 206.93 |
| ePC(36:0) | 0.43 | 0.52 |
| ePC(38:5) | 7.79 | 10.13 |
| LPC(18:0) | 122.02 | 142.51 |
| LPC(22:5) | 3.60 | 5.26 |
| PC(36:1) | 26.42 | 32.92 |
| PC(40:4) | 4.92 | 6.46 |
| PC(40:5) | 18.06 | 25.97 |
| PC(40:8) | 7.99 | 12.89 |
| PC(42:10) | 1.06 | 2.09 |
| PC(42:6) | 0.76 | 1.08 |
| PC(42:7) | 0.87 | 1.36 |
| PC(42:9) | 0.88 | 1.35 |
| PI(34:1) | 0.96 | 1.44 |
| PI(38:4) | 77.68 | 99.89 |
| PI(38:5) | 4.50 | 6.20 |

The plasma concentrations of these specific polar lipid species monitored could be increased significantly using increased amounts of B vitamins.

Example 4

Combined Dietary Folate, Vitamin B12, and Vitamin B6 Intake Increases Plasma Levels of Specific Polar Lipid Species Methods Animals A total of 24 male Sprague-Dawley rats (Crl:CD(SD)) were obtained from Charles River, Sulzfeld, Germany. Animals aged 6-8 weeks on arrival were housed in groups in a temperature- and light-controlled room, under 12 h light-12 h dark cycles. Rats had free access to food and water. Body weight was registered once a week. All animal experimental protocols were conducted in accordance with international and national laws and institutional guidelines and approved by the local ethics committee, i.e. DEC Consult, Bilthoven, The Netherlands.

Diets

Two different diets with increasing folate, vitamin B12, and vitamin B6 contents were used: 1) Bvitamin-poor and 2) Bvitamin-high. Diets were AIN-93 M based [1], isoenergetic, and identical with respect to their protein, carbohydrate, fat, fiber, and mineral contents. All diets were devoid of any measurable amounts of DHA. The vitamin mix (AIN-93-VX) [1] was prepared without folic acid, cyanocobalamin, and pyridoxine; these vitamins were subsequently supplemented accordingly. Diets were formulated with vitamin-free, ethanol-precipitated casein (Harlan Teklad, Madison, Wis., USA) and were manufactured by Ssniff Spezialdiäten, Soest, Germany.

The Bvitamin-poor diet contained low amounts of folate (<0.1 mg/kg), vitamin B12 (<1.0 μg/kg), and vitamin B6 (<0.6 mg/kg). No sulfathiazole drugs were added to the diet and therefore a limited amount of folate was still expected to be provided by the gut flora. Vitamin B12 deficiency in the rat is difficult to achieve because of considerable endogenous storage of this vitamin. To attain a moderate reduction of endogenous vitamin B12, the Bvitamin-poor was supplemented with 50 g/kg pectin (polygalacturonic acid, high methoxyl, Obipekting®, NF/USP Citrus; TEFCO FoodIngredients, Bodegraven, The Netherlands), which binds vitamin B12 in the intestine, making it less bioavailable [2]. Pectin consequently promotes depletion of endogenous vitamin B12 through the enterohepatic circulation the vitamin. Since pectin could affect food intake [3], all two diets were supplemented with pectin to maintain uniform intakes of the diets. Pectin has minimal effects on vitamin B12 status when the diet contains adequate amounts of this vitamin [2].

The vitamin B-high diet provided 1600%, respectively, of the requirements for each of the three vitamins according to the National Research Council report on the nutrient requirements of laboratory animals [4]. The exact dietary levels of the three Bvitamins in each experimental diet are indicated in Table 1.

TABLE 5

Folate, vitamin B12, and vitamin B6 content of the experimental diets

| Diet description | % of recommended levels [4] | Calculated dietary levels | | |
|---|---|---|---|---|
| | | Folate (folic acid) | Vitamin B12 (cyanocobalamin) mg/kg diet | Vitamin B6 (pyridoxine-HCL) |
| B vitamin: poor | ~0% | <0.1 | <0.001 | <0.6 |
| B vitamin: high | 1600% | 16.0 | 0.80 | 96.0 |

Experimental Design

Animals were randomized into the two experimental groups according to their body weights at the start of the intervention period. Subsequently, rats were fed one of the two experimental diets for 4 weeks.

Tissue Preparation

After the supplementation period, animals that had been feed-deprived for 3-4 hours were killed by inhalation of isoflurane vaporized in medicinal air and subsequent decapitation by guillotine. Trunk blood was collected through a funnel into EDTA-containing tubes. After centrifugation at 1750×g for 10 min, plasma was aspirated for subsequent analyses.

Plasma Polar Lipid Species

Plasma samples were analyzed for lipid profiles at the Kansas Lipidomics Research Center using electrospray ionization tandem mass spectrometry (ESI-MS/MS).

Results

TABLE 6

Plasma concentrations of specific polar lipid species (μM)

| Parameter | B vitamin poor | B vitamin high |
|---|---|---|
| C20:4 CE | 3150.15 | 5727.49 |
| C22:6 CE | 59.62 | 132.26 |
| ePC(36:5) | 2.72 | 3.85 |
| ePC(38:0) | 2.12 | 3.53 |
| ePC(38:6) | 2.57 | 3.83 |
| ePC(40:5) | 2.08 | 3.17 |
| ePC(40:6) | 2.29 | 3.71 |
| ePE(40:6) | 0.65 | 0.97 |
| LPC(20:5) | 0.78 | 1.08 |
| LPC(22:6) | 10.15 | 17.81 |
| PC(36:5) | 14.15 | 18.27 |
| PC(36:6) | 1.08 | 1.66 |
| PC(38:0) | 1.32 | 2.01 |
| PC(38:5) | 108.78 | 174.86 |
| PC(38:6) | 82.80 | 131.48 |
| PC(40:6) | 42.26 | 78.73 |
| PC(40:7) | 10.18 | 17.80 |
| PI(40:5) | 2.90 | 5.13 |
| PI(40:6) | 2.75 | 4.58 |
| C18:3 CE | 33.48 | 59.77 |
| ePC(38:4) | 12.10 | 18.68 |
| ePC(40:4) | 3.96 | 5.81 |
| LPC(18:3) | 1.55 | 2.12 |
| LPC(20:4) | 121.37 | 182.45 |
| PC(38:4) | 338.00 | 588.56 |
| PC(42:8) | 1.05 | 1.73 |
| C16:1 CE | 113.17 | 181.77 |
| ePC(36:0) | 0.43 | 0.67 |
| ePC(38:5) | 7.79 | 11.48 |
| LPC(18:0) | 122.02 | 172.13 |
| LPC(22:5) | 3.60 | 6.62 |
| PC(36:1) | 26.42 | 37.50 |
| PC(40:4) | 4.92 | 7.52 |
| PC(40:5) | 18.06 | 32.10 |
| PC(40:8) | 7.99 | 15.16 |
| PC(42:10) | 1.06 | 2.56 |
| PC(42:6) | 0.76 | 1.29 |
| PC(42:7) | 0.87 | 1.43 |
| PC(42:9) | 0.88 | 1.65 |
| PI(34:1) | 0.96 | 1.64 |
| PI(38:4) | 77.68 | 107.27 |
| PI(38:5) | 4.50 | 6.20 |

The plasma concentrations of these specific polar lipid species monitored could be increased significantly using increased amounts of B vitamins.

References

1. Reeves P G, Nielsen F H, Fahey G C Jr: "*AIN-93 purified diets for laboratory rodents: final report of the American Institute of Nutrition ad hoc writing committee on the reformulation of the AIN-76A rodent diet*". J Nutr 1993, 123:1939-1951.
2. Cullen R W, Oace S M: "*Dietary pectin shortens the biologic half-life of vitamin B12 in rats by increasing fecal and urinary losses*" J Nutr 1989, 119:1121-1127.
3. Hove E L, King S: "*Effects of pectin and cellulose on growth, feed efficiency, and protein utilization, and their contribution to energy requirement and cecal VFA in rats*" J Nutr 1979, 109:1274-1278.
4. National Research Council: *Nutrient requirements of laboratory animals, Fourth Revised Edition edn.* Washington: National Academic Press; 1995.

Example 5

Clinical Study

In the present intervention plasma concentrations of a selected range of phosphatidylcholine [PC] species were monitored. The study was a 24-week, randomized, controlled, double-blind study, conducted at 27 study centers. Drug-naive patients with mild AD (MMSE scores≥20) and diagnosis of probable AD according to the NINCDS-ADRDA criteria, were randomly assigned (1:1) to the composition including the components according to table 3, or an iso-caloric control product. The duration of intervention was 24 weeks.

TABLE 7

Nutritional composition used in Example 5 clinical trial

| component | Amount per daily dose* |
|---|---|
| EPA | 300 mg |
| DHA | 1200 mg |
| Phospholipids** | 106 mg |
| Choline | 400 mg |
| UMP | 625 mg |
| Vitamin E (alpha-TE) | 40 mg |
| Vitamin C | 80 mg |
| Selenium | 60 μg |
| Vitamin B12 | 3 μg |
| Vitamin B6 | 1 mg |
| Folic acid | 400 μg |

*125 ml, daily dose. TE = tocopherol equivalents.
**Source: Lecithin. Does not contain significant amount of phosphatidylcholine diacyl C36:6 [PC aa C36:6], PC aa C38:0, PC aa C38:6, PC aa C40:6 and PC acyl-alkyl C40:6 [PC ae C40:6]

Baseline and 24-week plasma samples of the subjects taking the intervention product were analyzed for plasma polar lipid profile at the Kansas Lipidomics Research Center using electrospray ionization tandem mass spectrometry (ESI-MS/MS). Phospholipid concentrations were compared between baseline and 24 weeks using T-test comparison. Only polar lipid species showing significant increase from baseline or significant decrease from baseline are reported.

Results

Plasma Polar Lipid Concentrations

The polar lipid plasma concentrations at baseline and at 24 weeks are given in Table 8.

TABLE 8

Plasma polar lipid concentration (nM; mean ± s.d.) in subjects taking the intervention product (n = 47) at baseline and after 24 weeks of intervention.
Intervention product

| Polar lipid | Baseline | 24-week | Effect |
|---|---|---|---|
| C20:4 CE | 1094.03 | 1208.72 | Increase |
| C22:6 CE | 116.16 | 280.76 | Increase |
| ePC(36:5) | 10.11 | 11.52 | Increase |
| ePC(38:0) | 2.86 | 4.57 | Increase |
| ePC(38:6) | 6.61 | 10.54 | Increase |
| ePC(40:5) | 8.26 | 9.08 | Increase |
| ePC(40:6) | 4.67 | 7.94 | Increase |
| ePE(40:6) | 0.58 | 0.99 | Increase |
| LPC(20:5) | 0.77 | 1.39 | Increase |
| LPC(22:6) | 1.37 | 2.65 | Increase |
| PC(36:5) | 28.64 | 49.32 | Increase |
| PC(36:6) | 1.62 | 2.28 | Increase |
| PC(38:0) | 4.89 | 6.32 | Increase |
| PC(38:5) | 50.43 | 59.98 | Increase |
| PC(38:6) | 70.71 | 151.85 | Increase |
| PC(40:6) | 26.84 | 60.42 | Increase |
| PC(40:7) | 5.74 | 8.67 | Increase |
| PI(40:5) | 0.83 | 1.03 | Increase |
| PI(40:6) | 1.17 | 2.81 | Increase |
| C16:0 CE | 466.57 | 528.01 | Increase |
| C18:2 CE | 6298.16 | 6782.25 | Increase |
| C20:5 CE | 233.35 | 557.18 | Increase |
| C22:5 CE | 9.75 | 11.24 | Increase |
| DSM(18:0) | 1.79 | 2.52 | Increase |
| ePC(32:1) | 4.43 | 4.67 | Increase |
| ePC(32:2) | 0.78 | 0.90 | Increase |
| ePC(34:0) | 1.58 | 1.80 | Increase |
| ePE(38:6) | 0.95 | 1.44 | Increase |
| LPE(22:6) | 0.62 | 1.11 | Increase |
| PA(34:3) | 0.33 | 0.36 | Increase |
| PC(44:2) | 0.33 | 0.39 | Increase |
| PE(36:0) | 0.34 | 0.49 | Increase |
| PE(38:0) | 0.40 | 0.78 | Increase |
| PE(38:6) | 5.02 | 8.09 | Increase |
| PE(40:6) | 3.22 | 5.56 | Increase |
| PE(40:7) | 0.84 | 1.24 | Increase |
| PI(38:6) | 0.55 | 1.18 | Increase |
| SM(16:0) | 270.43 | 290.29 | Increase |
| SM(18:0) | 57.27 | 60.67 | Increase |
| SM(22:0) | 3.09 | 5.06 | Increase |
| SM(24:0) | 58.11 | 63.47 | Increase |
| SM(24:1) | 151.66 | 168.89 | Increase |
| C19:0 CE | 12.29 | 9.31 | Decrease |
| C19:1 CE | 121.39 | 76.09 | Decrease |
| C20:0 CE | 90.66 | 49.23 | Decrease |
| C20:1 CE | 48.22 | 28.72 | Decrease |
| C20:3 CE | 136.94 | 124.01 | Decrease |
| ePC(36:1) | 14.03 | 11.42 | Decrease |
| ePC(38:1) | 8.83 | 8.36 | Decrease |
| ePC(38:2) | 9.50 | 8.19 | Decrease |
| ePC(38:3) | 11.70 | 6.78 | Decrease |
| ePC(40:2) | 3.48 | 3.00 | Decrease |
| ePC(40:3) | 5.59 | 3.35 | Decrease |
| LPC(20:3) | 1.84 | 1.41 | Decrease |
| PC(34:3) | 17.58 | 14.23 | Decrease |
| PC(36:3) | 133.07 | 110.74 | Decrease |
| PC(38:1) | 1.51 | 1.02 | Decrease |
| PC(38:2) | 3.94 | 1.83 | Decrease |
| PC(40:3) | 1.89 | 1.31 | Decrease |
| PE(34:1) | 1.53 | 1.10 | Decrease |
| PE(34:2) | 2.45 | 1.75 | Decrease |
| PE(36:1) | 1.23 | 1.04 | Decrease |
| PE(36:2) | 7.23 | 5.57 | Decrease |
| PE(36:3) | 2.20 | 1.47 | Decrease |
| PE(36:4) | 3.56 | 2.64 | Decrease |
| PE(38:3) | 0.74 | 0.49 | Decrease |
| PE(38:4) | 8.96 | 6.56 | Decrease |
| PE(40:4) | 0.39 | 0.33 | Decrease |
| PE(40:5) | 0.69 | 0.52 | Decrease |
| PI(36:3) | 1.97 | 1.57 | Decrease |
| PI(38:3) | 4.77 | 4.00 | Decrease |
| PS(38:4) | 0.95 | 0.55 | Decrease |

CONCLUSIONS

Overall, the plasma concentrations of specific polar lipids monitored over the intervention period, showed a significant increase after taking the intervention product for 24 weeks (see table 8). Concentrations of other specific polar lipids decrease as a result of the intervention product. These results indicate that specific polar lipids can be increased and other specific polar lipids can be decreased by intervention product as claimed in the invention.

The invention claimed is:
1. A method for treating, inhibiting, suppressing, and/or decreasing impaired plasma levels of one or more polar lipids selected from the group consisting of C16:1CE; C18:3CE; C20:4CE; PI(34:1); PI(38:2); PI(38:4); C16:0CE; C18:2CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5CE; C22:6CE; aePC(38:6); aePC(40:6); aePE(40:6); PC(36:6); PC(38:6); PC(40:6); PC(42:6); PI(40:6); C22:5CE; aePE(38:6); lPE(22:6); PE(38:6); PE(40:6); PI(38:6); PC(40:7); PC(40:8); PC(42:10); PC(42:7); PC(42:8); PC(42:9); PE(40:7); lPC(22:6); C19:0CE; C19:1CE; C20:0CE; C20:1CE; C20:3CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5) in a subject with Alzheimer's Disease (AD) or mild cognitive impairment (MCI), the method comprising administering to the subject a composition comprising:
(a) at least one B vitamin selected from the group consisting of vitamin B6, vitamin B12 and vitamin B9; and
(b) one or more of uridine and cytidine, or salts, phosphates or esters thereof.

2. The method according to claim 1, wherein the composition comprises at least two B vitamins selected from the group consisting of vitamin B6, vitamin B12 and vitamin B9.

3. The method according to claim 2, wherein the composition comprises vitamin B6, vitamin B12 and vitamin B9.

4. The method according to claim 1, wherein the composition comprises per daily dosage or per 100 ml, at least one of:
0.5-10000 µg vitamin B12;
0.5-100 mg vitamin B6; and
100-5000 µg folic acid.

5. The method according to claim 3, wherein the composition comprises per daily dosage or per 100 ml:
0.5-10000 µg vitamin B12;
0.5-100 mg vitamin B6; and
100-5000 µg folic acid.

6. The method according to claim 1, wherein the composition comprises per daily dosage or per 100 ml, 0.5-100 mg vitamin B6, and 100-5000 µg folic acid.

7. The method according to claim 1, wherein the plasma polar lipids are lPC 22:6 and/or PC 40:6.

8. The method according to claim 1, wherein the composition comprises one or more of uridine or salts, phosphates or esters thereof.

9. The method according to claim 1, wherein the composition further comprises a lipid fraction comprising at least one of docosahexaenoic acid (22:6; DHA), eicosapentaenoic acid (20:5; EPA) and docosapentaenoic acid (22:5; DPA), or esters thereof.

10. The method according to claim 1, wherein the composition further comprises, per daily dose or per 100 ml composition, at least 500 mg of DHA, and at least 50 mg of uridine.

11. The method according to claim 1, wherein the composition comprises, per daily dose or per 100 ml composition:
0.5-10000 µg vitamin B12;
0.5-100 mg vitamin B6;
100-5000 µg folic acid;
100-500 mg EPA,
1000-1500 mg DHA,
50-600 mg phospholipids,
200-600 mg choline,
400-800 mg UMP (uridine monophosphate),
20-60 mg vitamin E (alpha-TE),
60-100 mg vitamin C, and
40-80 µg selenium.

12. The method according claim 1, wherein the subject is an elderly of at least 50 years of age, and not suffering from any cognitive deficits.

13. A method for treating, inhibiting, suppressing, and/or decreasing impaired plasma levels of one or more phosphatidylcholines (PCs) selected from the group consisting of phosphatidylcholine diacyl C36:6[PC aa C36:6], phosphatidylcholine diacyl C38:0[PC aa C38:0], phosphatidylcholine diacyl C38:6[PC aa C38:6], phosphatidylcholine diacyl C40:6[PC aa C40:6] and phosphatidylcholine acyl-alkyl C40:6[PC ae C40:6] in a AD or MCI subject, the method comprising administering to the subject a comprising:
(a) at least one B vitamin selected from the group consisting of vitamin B6, vitamin B12 and vitamin B9; and
(b) one or more of uridine and cytidine, or salts, phosphates or esters thereof.

14. The method according to claim 13, wherein the composition comprises at least two B vitamins selected from the group consisting of vitamin B6, vitamin B12 and vitamin B9.

15. The method according to claim 14, wherein the composition comprises vitamin B6, vitamin B12 and vitamin B9.

16. The method according to claim 13, wherein the one or more phosphatidylcholines are at least two phosphatidylcholine species selected from the group consisting of phosphatidylcholine diacyl C36:6[PC aa C36:6], phosphatidylcholine diacyl C38:0[PC aa C38:0], phosphatidylcholine diacyl C38:6[PC aa C38:6], phosphatidylcholine diacyl C40:6[PC aa C40:6] and phosphatidylcholine acyl-alkyl C40:6[PC ae C40:6].

17. The method according to claim 13, wherein the one or more phosphatidylcholine species is selected from the group consisting of phosphatidylcholine diacyl C36:6[PC aa C36:6], phosphatidylcholine diacyl C38:6[PC aa C38:6], phosphatidylcholine diacyl C40:6[PC aa C40:6] and phosphatidylcholine acyl-alkyl C40:6[PC ae C40:6].

18. The method according to claim 17, wherein the polar lipids are phosphatidylcholine diacyl C40:6[PC aa C40:6] and/or phosphatidylcholine acyl-alkyl C40:6[PC ae C40:6].

19. The method according to claim 13, further comprising monitoring plasma PC levels in the subject before and/or after administration.

20. A method for treating, inhibiting, suppressing, and/or decreasing impaired plasma polar lipid levels in a AD or MCI subject, comprising:
(a) analyzing plasma levels of at least one plasma polar lipid in a subject, wherein the plasma polar lipid is selected from the group consisting of C16:1CE; C18:3CE; C20:4CE; PI(34:1); PI(38:2); PI(38:4); C16:0CE; C18:2CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:5); PI(40:5); C20:5CE; C22:6CE;

aePC(38:6); aePC(40:6); aePE(40:6); PC(36:6); PC(38:6); PC(40:6); PC(42:6); PI(40:6); C22:5CE; aePE(38:6); lPE(22:6); PE(38:6); PE(40:6); PI(38:6); PC(40:7); PC(40:8); PC(42:10); PC(42:7); PC(42:8); PC(42:9); PE(40:7); lPC(22:6); C19:0CE; C19:1CE; C20:0CE; C20:1CE; C20:3CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5);

(b) selecting a subject having an impaired plasma level of one or more of the plasma polar lipids;

(c) administering to the selected subject a composition comprising:

(i) at least one B vitamin selected from the group consisting of vitamin B6, vitamin B12 and vitamin B9; and (ii) one or more of uridine and cytidine, or salts, phosphates or esters thereof.

21. The method according to claim 20, wherein the composition comprises vitamin B6, vitamin B12 and vitamin B9.

22. The method according to claim 20, wherein the composition further comprises one or more of uridine, or salts, phosphates or esters thereof.

23. A method for treating, inhibiting, suppressing, and/or decreasing impaired plasma polar lipid levels in a AD or MCI subject, comprising:

(a) analyzing plasma levels of at least one plasma polar liquid in a subject, wherein the plasma polar liquid is selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM(18:0); aePC(32:1); aePC(32:2); aePC(34:0); PC(44:26); SM(16:0); SM(18:0); SM(22:0); SM(24:06); SM(24:1); aePC(36:5); aePC(38:5); aePC(40:5); lPC(20:5); lPC(22:5); PC(36:5); PC(38:5); PC(40:5); PI(38:5); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); lPE(22:6); PE(38:6); PE(40:6); PI(38:6); PC(40:7); PC(40:8); PC(42:10); PC(42:7); PC(42:8); PC(42:9); PE(40:7); lPC(22:6); C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5);

(b) selecting a subject having an impaired plasma level of one or more of the plasma polar lipids;

(c) administering to the selected subject a composition comprising:

(i) at least one B vitamin selected from the group consisting of vitamin B6, vitamin B12 and vitamin B9 ; and (ii) at least one of docosahexaenenoic acid (22:6; DHA), eicosapentaenoic acid (20:5; EPA) and docosapentaenoic acid (22:5; DPA), or esters thereof.

24. The method according to claim 23, wherein the composition comprises docosahexaenoic acid (22:6; DHA) or an ester thereof.

25. The method according to claim 13, wherein the composition comprises one or more of uridine or salts, phosphates or esters thereof.

26. A method for treating, inhibiting, suppressing, and/or decreasing impaired plasma levels of one or more phosphatidylcholines (PCs) selected from the group consisting of phosphatidylcholine diacyl C36:6 [PC aa C36:6], phosphatidylcholine diacyl C38:0 [PC aa C38:0], phosphatidylcholine diacyl C38:6 [PC aa C38:6], phosphatidylcholine diacyl C40:6 [PC aa C40:6] and phosphatidylcholine acyl-alkyl C40:6 [PC ae C40:6] in a AD or MCI subject, the method comprising administering to the subject a comprising:

(a) at least one B vitamin selected from the group consisting of vitamin B6, vitamin B12 and vitamin B9; and (b) at least one of docosahexaenoic acid (22:6; DHA), eicosapentaenoic acid (20:5; EPA) and docosapentaenoic acid (22:5; DPA), or esters thereof.

27. The method according to claim 25, wherein the composition comprises docosahexaenoic acid (22:6; DHA) or an ester thereof.

28. A method for treating, inhibiting, suppressing, and/or decreasing impaired plasma levels of one or more polar lipids selected from the group consisting of C16:1 CE; C18:3 CE; C20:4 CE; PI(34:1); PI(38:2); PI(38:4); C16:0 CE; C18:2 CE; PA(34:3); PE(36:0); PE(38:0); aePC(36:0); aePC(38:0); aePC(38:4); aePC(40:4); lPC(18:0); lPC(18:3); lPC(20:4); PC(36:1); PC(38:0); PC(38:4); PC(40:4); DSM (18:0); aePC(32:1); aePC(32:2); aePC(34:0); PC(44:2); SM(16:0); SM(18:0); SM(22:0); SM(24:0); SM(24:1); aePC(36:5); aePC(38:5); aePC(40:5); lPC(20:5); lPC(22:5); PC(36:5); PC(38:5); PC(40:5); PI(38:56); PI(40:5); C20:5 CE; C22:6 CE; aePC(38:6); aePC(40:6); aePE(40:6); PC(36:6); PC(38:6); PC(40:6); PC(42:6); PI(40:6); C22:5 CE; aePE(38:6); lPE(22:6); PE(38:6); PE(40:6); PI(38:6); PC(40:7); PC(40:8); PC(42:10); PC(42:7); PC(42:8); PC(42:9); PE(40:7); lPC(22:6); C19:0 CE; C19:1 CE; C20:0 CE; C20:1 CE; C20:3 CE; PE(34:1); PE(34:2); PE(36:1); PE(36:2); PE(36:3); PE(36:4); PE(38:3); PE(38:4); PE(40:4); PI(36:3); PI(38:3); PS(38:4); aePC(36:1); aePC(38:1); aePC(38:2); aePC(38:3); aePC(40:2); aePC(40:3); lPC(20:3); PC(34:3); PC(36:3); PC(38:1); PC(38:2); PC(40:3); and PE(40:5) in a subject with Alzheimer's Disease (AD) or mild cognitive impairment (MCI), the method comprising administering to the subject a composition comprising:

(a) at least one B vitamin selected from the group consisting of vitamin B6, vitamin B12 and vitamin B9; and (b) at least one of docosahexaenoic acid (22:6; DHA), eicosapentaenoic acid (20:5; EPA) and docosapentaenoic acid (22:5; DPA), or esters thereof.

29. The method according to claim 28, wherein the composition comprises docosahexaenoic acid (22:6; DHA) or an ester thereof.

* * * * *